(12) United States Patent
Ueno et al.

(10) Patent No.: US 7,226,412 B2
(45) Date of Patent: Jun. 5, 2007

(54) ENDOSCOPE SYSTEM USING NORMAL LIGHT AND FLUORESCENCE

(75) Inventors: Hitoshi Ueno, Hachioji (JP); Takeshi Ozawa, Sagamihara (JP); Kazunari Nakamura, Zama (JP); Isami Hirao, Hachioji (JP); Hiroshi Ibe, Yokohama (JP); Koichi Yoshimitsu, Hino (JP); Yuichi Morizane, Hachioji (JP); Mamoru Kaneko, Hanno (JP); Shunya Akimoto, Hachioji (JP); Masaki Terakubo, Sagamihara (JP); Katsuichi Imaizumi, Hino (JP); Nobuyuki Doguchi, Hino (JP); Sakae Takehana, Sagamihara (JP); Kazuhiro Gono, Sagamihara (JP)

(73) Assignee: Olympus Corporation (JP)

( * ) Notice: Subject to any disclaimer, the term of this patent is extended or adjusted under 35 U.S.C. 154(b) by 451 days.

(21) Appl. No.: 10/853,846

(22) Filed: May 25, 2004

(65) Prior Publication Data

US 2004/0215060 A1    Oct. 28, 2004

Related U.S. Application Data

(62) Division of application No. 10/146,389, filed on May 14, 2002, now Pat. No. 7,172,553.

(30) Foreign Application Priority Data

| May 16, 2001 | (JP) | ............................. 2001-146755 |
| Oct. 22, 2001 | (JP) | ............................. 2001-323936 |
| Oct. 22, 2001 | (JP) | ............................. 2001-323937 |

(51) Int. Cl.
*A61B 1/05* (2006.01)
*A61B 1/06* (2006.01)

(52) U.S. Cl. ....................... 600/178; 600/181; 600/118

(58) Field of Classification Search ................ 600/160, 600/178, 109, 118, 181, 476–478
See application file for complete search history.

(56) References Cited

U.S. PATENT DOCUMENTS 4,768,089 A    8/1988    Kato (Continued)

FOREIGN PATENT DOCUMENTS

JP    5-37650    6/1993

(Continued)

OTHER PUBLICATIONS

Office Action issued by European Patent Office on Apr. 28, 2005 in connection with corresponding European patent application No. 02010242.2.

*Primary Examiner*—John P. Leubecker
(74) *Attorney, Agent, or Firm*—Ostrolenk, Faber, Gerb & Soffen, LLP

(57) ABSTRACT

An endoscope system in accordance with an embodiment of the present invention includes an endoscope with a monochrome image pickup device for capturing reflected light and fluorescence from the body cavity, an excitation light cut filter which is installed in front of the image pickup device for shielding excitation light, and an endoscope ID which includes information on the type of the endoscope. A light source unit includes a first switching filter that irradiates light including excitation light for a fluorescent image mode and a filter for generating continuous light for a normal-light image mode. The filters switch based between the fluorescent image mode and the normal-light image mode. A second switching filter with a limiting filter that limits certain wavelengths of excitation light of the first switching filter is provided. The limiting filters are switched according to the endoscope ID or observation state in the fluorescence mode. The excitation light cut filter shields excitation light generated by the first and second filters.

15 Claims, 27 Drawing Sheets

U.S. PATENT DOCUMENTS

| | | | |
|---|---|---|---|
| 5,001,556 A * | 3/1991 | Nakamura et al. | 348/70 |
| 5,647,368 A | 7/1997 | Zeng et al. | |
| 5,749,830 A * | 5/1998 | Kaneko et al. | 600/160 |
| 5,827,190 A | 10/1998 | Palcic et al. | 600/476 |
| 5,971,918 A * | 10/1999 | Zanger | 600/160 |
| 6,478,732 B2 * | 11/2002 | Adachi | 600/178 |
| 2002/0035330 A1 * | 3/2002 | Cline et al. | 600/476 |
| 2002/0161282 A1 * | 10/2002 | Fulghum | 600/160 |
| 2004/0186351 A1 * | 9/2004 | Imaizumi et al. | 600/160 |

FOREIGN PATENT DOCUMENTS

| | | |
|---|---|---|
| JP | 10-151104 | 6/1998 |
| JP | 10-201707 | 8/1998 |
| JP | 10-309282 | 11/1998 |
| JP | 2000-270265 | 9/2000 |
| JP | 2001-137174 | 5/2001 |

* cited by examiner

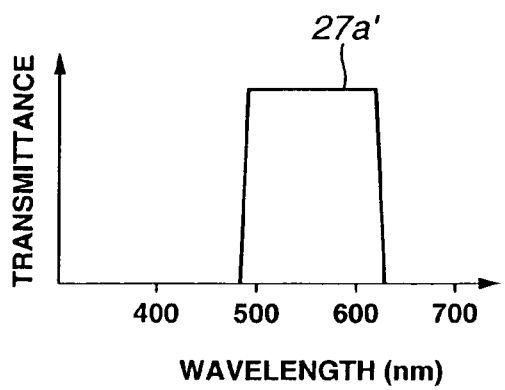
FIG.32A
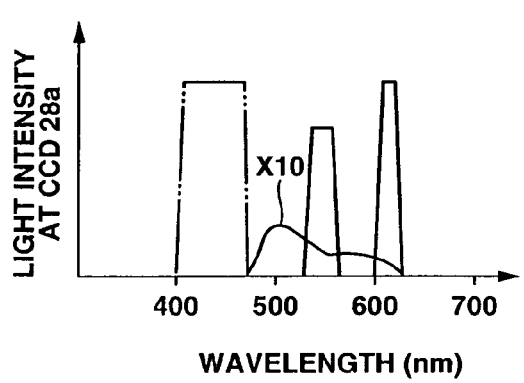
FIG.32B
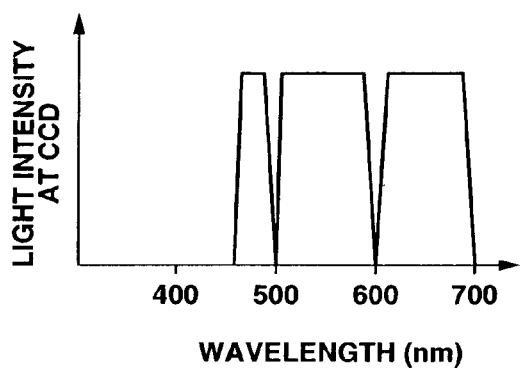
FIG.33A
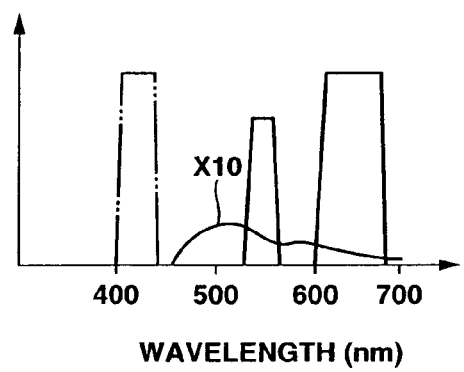
FIG.33B
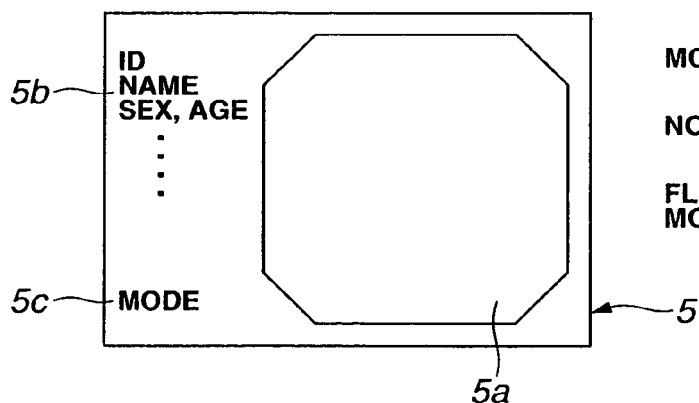
FIG.34A
FIG.34B
MODE
NORMAL MODE
FLUORESCENT : PRIORITY TO
MODE           BRIGHTNESS
             : DEPTH
               INFORMATION

ENDOSCOPE SYSTEM USING NORMAL LIGHT AND FLUORESCENCE

CROSS-REFERENCE TO RELATED APPLICATIONS

This application is a divisional of U.S. application Ser. No. 10/146,389 filed May 14, 2002 entitled ENDOSCOPE SYSTEM USING NORMAL LIGHT AND FLUORESCENCE now U.S. Pat. No. 7,172,553, which claims the benefit of Japanese Application Nos. 2001-146755 filed on May 16, 2001, 2001-323936 filed on Oct. 22, 2001 and 2001-323937 filed on Oct. 22, 2001 the contents of which are incorporated by this reference.

BACKGROUND OF THE INVENTION

1. Field of the Invention

The present invention relates to an endoscope system using normal light and fluorescence for obtaining normal reflected light images and fluorescent images.

2. Description of the Related Art

Endoscopes are widely used today in the medical field and the industrial field. Particularly in the medical field, a technology to obtain images which make it easier to identify normal tissue and abnormal tissue has been proposed, in addition to an endoscope system for obtaining normal-light images using conventional white light.

For example, as a first prior art, Japanese Patent Laid-Open Publication No. 2001-137174 discloses a system for generating display signals mainly by reflecting the relative intensity of fluorescence to the color, and the intensity of a reference light to the luminance.

As a second prior art, Japanese Patent Laid-Open Publication No. 2000-270265 discloses a system for overlaying fluorescent images and background images.

As a third prior art, Japanese Patent Publication No. 5-37650 discloses a system for detecting an abnormal section of the respiratory metabolism of a human body using fluorescent images and reference images by reference light.

As a fourth prior art, Japanese Laid-Open Publication No. 10-309282 discloses a system for irradiating excitation light and obtaining images which make it easier to identify normal tissue and abnormal tissue by two fluorescent images with different wavelength bands and reflected images by excitation light.

In addition to these, the following are also prior art.

(a) U.S. Pat. No. 5,827,190

This patent discloses a system for creating fluorescent images and non-fluorescent images. Excitation light (400 to 450 nm) and illumination light (including 700 nm) are sequentially irradiated endoscopically, and fluorescent and reflected light generated from biological tissue are received by an image pickup device. These signals are displayed on a monitor such that pathologically affected tissue and normal tissue can be distinguished.

Or, the irradiation time of the above mentioned excitation light is set to longer than that of non-excitation light (illumination light). By building a CCD into the tip of the endoscope and by integrating the pixels of the CCD when fluorescent images are captured (when excitation light is irradiated), brightness (S/N) is improved.

(b) Japanese Patent Laid-Open Publication No. 10-151104

This patent discloses a system for sequentially displaying conventional-light images and fluorescent (infrared) images. A rotary filter for conventional-light images and a rotary filter for fluorescent images are arranged concentrically, and the rotary filters move depending on the mode (FIGS. 12 to. FIG. 17 of this gazette).

Also an optical aperture for transmitting the infrared light is installed at the tip of the endoscope, so in fluorescent mode, brightness can be improved since more infrared light transmits. With visible light, the opening (see FIG. 6 of this gazette) is restricted by the optical aperture, so ability of distinction becomes high.

(c) Japanese Patent Laid-Open Publication No. 10-201707

This patent discloses a system for sequentially displaying normal-light images and fluorescent images. It is disclosed that the filter which transmits the visible light and the filter which transmits the infrared light are selected by switching the mode (normal-light images and fluorescent images) for the rotary filters red and infrared, G and B, installed at the light source (FIG. 9 to FIG. 11 of this gazette).

In the first prior art, the intensity of the fluorescence emitted from a normal tissue differs depending on the patient, so the color tone of a normal tissue differs depending on the patient, and the identification of pathologically affected tissue and normal tissue may be difficult in some cases.

In the second prior art, reflected light has a wide band, so the function to obtain images, which make it easier to identify normal tissue and pathologically affected tissue, drops.

In the third prior art, a regression line to the target tissue is derived using the fluorescent images and reference images, but only the wavelengths of the reference images are matched with the wavelengths of the fluorescent images, so the identification function between the normal tissue and pathologically affected tissue may not be sufficiently performed.

The fourth prior art has a complicated configuration.

SUMMARY OF THE INVENTION

It is an object of the present invention to provide an endoscope system which can obtain images for easily identifying normal tissue and pathologically affected tissue with a simple configuration.

It is another object of the present invention to provide an endoscope system which allows observing both normal-light images and fluorescent images.

The present invention is an endoscope system comprising a light source for illuminating illumination light having two different wavelength bands and excitation light for exciting fluorescence; image capturing means for capturing two reflected light images by reflected light when the illumination light is irradiated onto a biological tissue and is reflected, and a fluorescent image by fluorescence excited by the excitation light; image processing means for processing the two reflected light images and a fluorescent image and a creating processed image; and display means for displaying the processed images, wherein when the processed images are distributed on spatial coordinates where three axes are the intensities of two different reflected lights and the fluorescence from the biological tissue, the wavelengths of the reflected lights and the fluorescence are selected such that the normal tissue and the pathologically affected tissue are separated on the three axes on the spatial coordinates, and the above mentioned image processing means further comprises means of inputting three signals of the fluorescent image and the two reflected light images, and axial conversion means for operating the signals and converting them into signals comprised of three color components so that luminance and/or hue differ between a normal tissue and a pathologically affected tissue, and images of the pathologically affected tissue enter within a specific range of hue, so as to obtain images which make it easier to identify the normal tissue and the pathologically affected tissue.

BRIEF DESCRIPTION OF THE DRAWINGS

FIG. 1 to FIG. 15 are drawings related to the first embodiment, wherein FIG. 1 is a block diagram depicting a general configuration of the endoscope system of the first embodiment;

FIG. 2 is a diagram depicting a configuration of a switching filter where a filter for normal-light observation and a filter for fluorescent observation are installed;

FIG. 4 is a block diagram depicting a configuration of the image processing circuit;

FIG. 6 is a diagram depicting the distribution of the normal sections and pathologically affected sections which are plotted on spatial coordinates, where three axes are the fluorescence intensity and the two reflected light intensities;

FIG. 7 is a diagram depicting the change of ability of distinction with respect to the central wavelength of the second reflected light when the wavelength of the first reflected light is assumed to be a parameter;

FIG. 8 is a diagram depicting the change of ability of distinction with respect to the central wavelength of the second reflected light when the wavelength width of the first reflected light is assumed to be a parameter;

FIG. 9 is a chromaticity diagram depicting the distribution of the normal sections and the pathologically affected sections when the matrix element is set as the formula 2;

FIG. 10 is a chromaticity diagram depicting the distribution of the normal sections and the pathologically affected sections when the matrix element is set as the formula 3;

FIG. 11 is a chromaticity diagram depicting the distribution of the normal sections and the pathologically affected sections when the matrix element is set as the formula 4;

FIG. 12 is a chromaticity diagram depicting the distribution of the normal sections and the pathologically affected sections when the matrix element is set as the formula 5;

FIG. 13 is a diagram depicting the operation area by the image processing circuit;

FIG. 14 is a block diagram depicting a configuration of the image processing circuit in the first variant form;

FIG. 15 is a block diagram depicting a configuration of the image processing circuit in the second variant form;

FIG. 17 is a block diagram depicting a configuration of the image processing circuit according to the third embodiment, and FIG. 18 is a diagram depicting the input/output characteristic of the enhancement conversion table;

FIG. 19 is a block diagram depicting a general configuration of the endoscope system of the third embodiment;

FIG. 20 is a block diagram depicting the image processor;

FIG. 21 is a diagram depicting a display example of the fluorescent image on a monitor;

FIG. 22 is a diagram depicting the screen to input and set the parameters of the matrix circuit;

FIG. 23 is a block diagram depicting a configuration of the image processor in the first variant form;

FIG. 24 is a block diagram depicting a configuration of the image processor in the second variant form;

FIG. 25 is a block diagram depicting a configuration of the image processor in the third variant form;

FIG. 26 to FIG. 37 are diagrams related to the fifth embodiment of the present invention, where FIG. 26 is a block diagram depicting a generation configuration of the endoscope system of the fifth embodiment;

FIG. 31 is a diagram depicting the light intensity characteristic with respect to the wavelength when the filter is changed and the image of skin is captured by a CCD for fluorescent observation in the fluorescent observation mode;

FIG. 32A and FIG. 32B are diagrams depicting the transmission characteristic of the excitation light cut filter of a variant form, and the light intensity characteristic when the image of skin is captured by a CCD for fluorescent observation using this excitation light cut filter in fluorescent observation mode;

FIG. 33A and FIG. 33B are diagrams depicting the light intensity characteristic of light to be received by a CCD when a white subject is observed in the normal-light observation mode, and when skin is observed in the fluorescent mode using the first scope;

FIG. 34A and FIG. 34B are diagrams depicting an image display example on a monitor, and the content of the mode to be displayed;

FIG. 35 is a block diagram depicting a general configuration of the endoscope system of the first variant form of the fifth embodiment;

FIG. 37 is a block diagram depicting a general configuration of the endoscope system of the second variant form of the fifth embodiment.

DESCRIPTION OF THE PREFERRED EMBODIMENTS

Embodiments of the present invention will now be described with reference to the accompanying drawings.

First Embodiment

The first embodiment of the present invention will be described with reference to FIG. 1 to FIG. 15.

Figure 1:
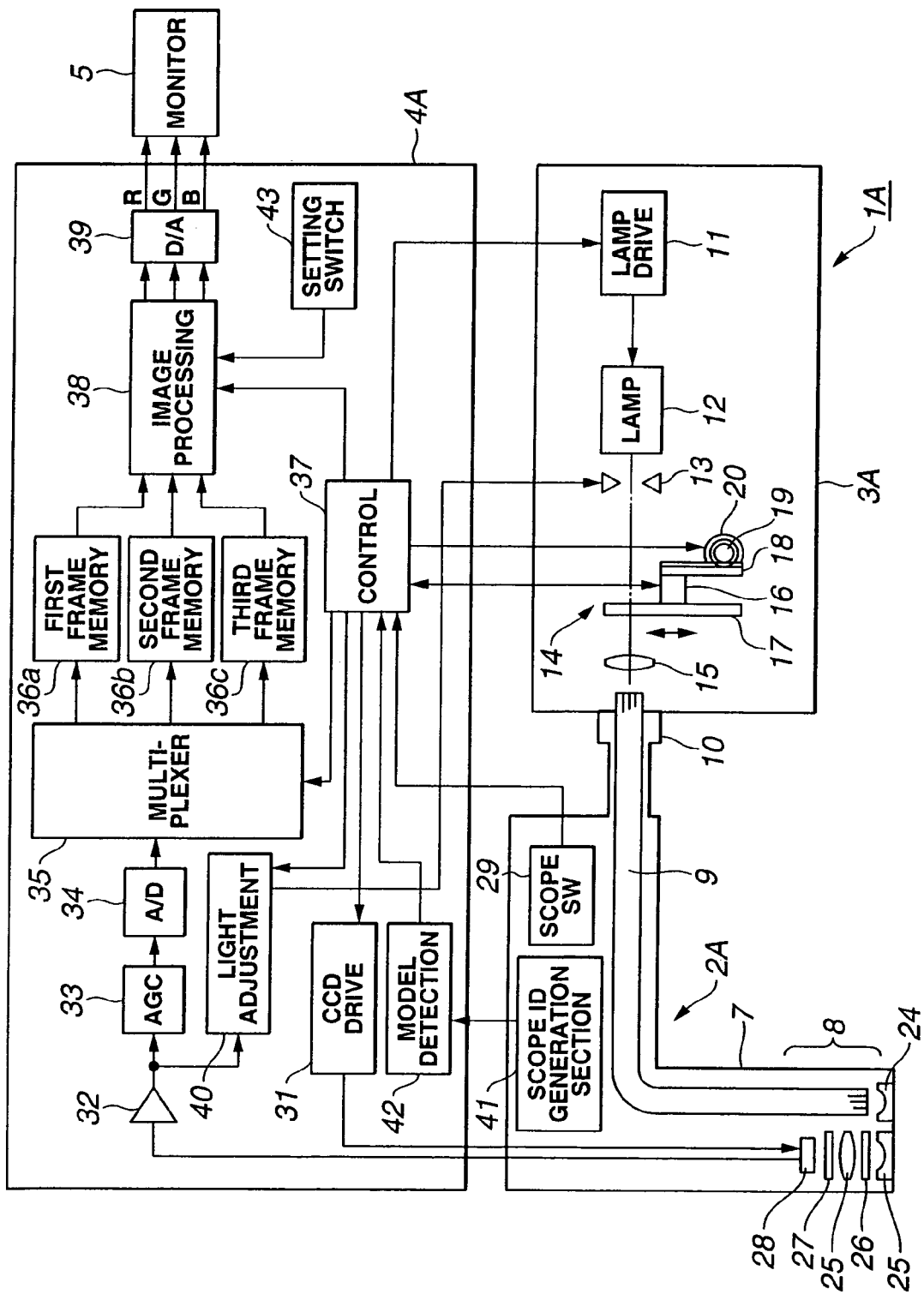

The endoscope system 1A, which has a normal-light observation mode and a fluorescent observation mode according to the first embodiment of the present invention shown in FIG. 1, comprises an electronic endoscope 2A which is inserted into a body cavity for observation, a light source unit 3A for emitting a light for normal-light observation and a light for excitation, a processor 4A for executing signal processing to create normal-light observation images and fluorescent images, and a monitor 5 for displaying images by normal light and images by fluorescence.

The electronic endoscope 2A has an elongated insertion section 7 which is inserted into a body cavity, and has illumination means and image capturing means which are enclosed in a tip 8 of the insertion section 7.

In the insertion section 7, a light guide fiber 9, for transmitting (guiding) excitation light and illumination light for normal-light observation, is inserted, and a connector 10 for the light source, which is installed at the incident end at the operator side of the light guide fiber 9, is removably connected to the light source unit 3A.

The light source unit 3A further comprises a lamp 12, which is driven to emit light by a lamp drive circuit 11, emits light including bands from infrared wavelength bands to visible light bands, a light source aperture 13 which is installed on the illumination light path by the lamp 12 and limits the light quantity from the lamp 12, a switching filter section 14 which is installed on the illumination light path, and a condenser lens 15 for condensing lights which pass through this switching filter section 14.

This switching filter section 14 further comprises a switching filter 17 which is rotated by a motor for rotation 16 and switching the filters to be placed on the optical path using a motor for moving 20, and the motor for moving 20 which moves the motor for rotation 16 and the switching filter 17 to a direction perpendicular to the optical axis by rotating a pinion 19 which screws into a rack 18 on the motor for rotation 16.

Figure 2:
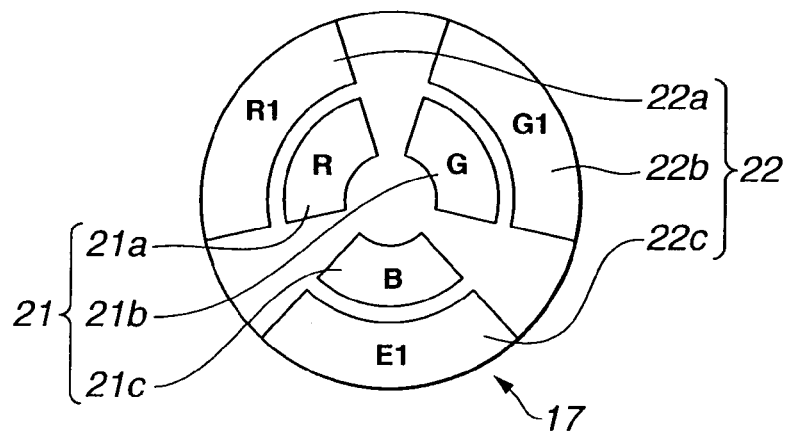

In the switching filter 17, an RGB filter for normal-light observation 21 and a filter for fluorescent observation 22 are installed concentrically at the inner circle side and the outer circle side, as shown in FIG. 2, and by driving the motor for moving 20, the filter for normal-light illumination 21 is set on the optical path to set the operation state in the normal-light image mode (also called normal-light mode), or the filter for normal-light illumination 21 is switched to the filter for fluorescent illumination 22 to set the operation state to fluorescent image mode (also called fluorescent mode).

The RGB filter 21 is provided with R, G and B filters 21a, 21b and 21c, for transmitting the wavelength band of R (red), G (green) and B (blue) respectively, so as to divide the RGB filter 21 into three equal sections in a circumferential direction, and each filter is sequentially and continuously inserted into the optical path respectively by the rotational driving of the motor for rotation 16.

Figure 3A:
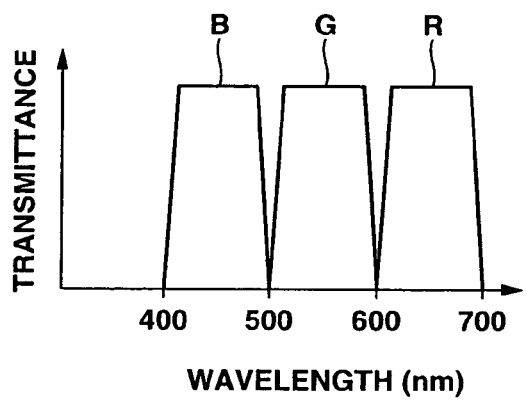
FIG. 3A to FIG. 3C are diagrams depicting the transmission characteristic of the filter for normal-light observation, filter for fluorescent observation, and excitation light cut filter.

The transmission characteristic of the R, G and B filters 21a, 21b and 21c is a filter characteristic for transmitting each wavelength band of 600 to 700 nm, 500 to 600 nm, and 400 to 500 nm respectively, as shown in FIG. 3A. In FIG. 3A and in other drawings, symbols R, G and B, corresponding to the respective filter transmission characteristic, are used instead of 21a, 21b and 21c. (This is the same for the later mentioned filter for fluorescent observation 22.)

The filter for fluorescent observation 22 is provided with R1, G1 and E1 filters 22a, 22b and 22c for transmitting the narrow band red (R1), narrow band green (G1) and narrow band excitation light (E1) respectively, so as to divide the filter 22 into three equal sections in a circumferential direction, and each filter is sequentially inserted into the optical path by the rotational driving of the motor for rotation 16.

Figure 3B:
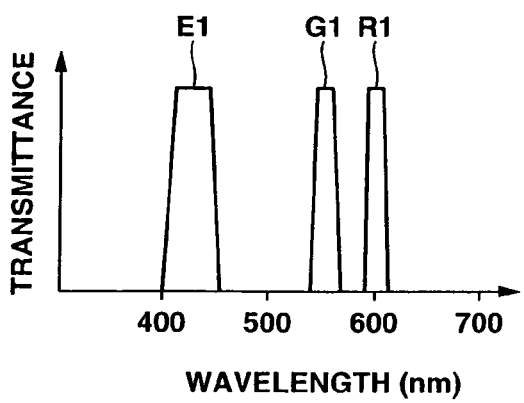

The transmission characteristic of R1, G1 and E1 filters 22a, 22b and 22c is a filter characteristic for transmitting each wavelength band of 590 to 610 nm, 540 to 560 nm and 390 to 445 nm respectively, as shown in FIG. 3B.

The illumination light from the light source unit 3A is transmitted (guided) to the tip of the insertion section 7 of the electronic endoscope 2A by the light guide fiber 9. This light guide fiber 9 transmits light for fluorescent observation and light for normal-light observation with low transmission loss. This light guide fiber 9 is made of multi-component glass fiber or of quartz fiber, for example.

The light transmitted to the tip face of the light guide fiber 9 is irradiated onto the observation target area in the body cavity via an illumination lens 24 installed on the illumination window facing the tip face.

An observation window is installed adjacent to the illumination window at the tip section 8, and an objective lens system 25 for forming an optical image, an aperture 26 for spatially limiting the incident light quantity in order to focus from a far point to a near point, an excitation light cut filter 27 for cutting excitation light, and an image pickup device for capturing fluorescent and reflected light images, such as a charge coupled device (CCD) 28, for capturing monochrome (or black and white) images, are installed in the observation window.

For the image pickup device for capturing fluorescent and reflected light images, a CMD (Charge Modulation Device), a C-MOS image pickup device, an AMI (Amplified MOS Imager) or a BCCD (Back Illuminated CCD) may be used instead of the CCD 28.

Figure 3C:
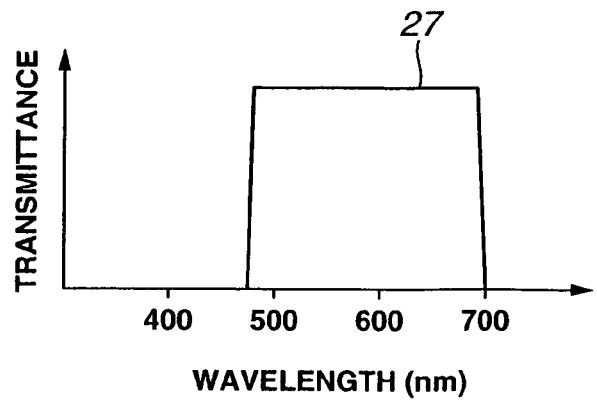

The excitation light cut filter 27 is a filter for shielding the excitation light which is used for generating fluorescence. FIG. 3C shows a characteristic of the excitation light cut filter 27. As FIG. 3C shows, the excitation light cut filter 27 has a characteristic to transmit a 470 to 700 nm wavelength band, that is, visible light excluding a part of the wavelength (400 to 470 nm) of the blue band.

This electronic endoscope 2A also has a scope switch 29 for controlling the instructions to select the fluorescent image mode and the normal-light image mode and for controlling the instructions for freeze and release, wherein the control signals are input to a control circuit 37, and the control circuit 37 executes control operation corresponding to the control signals.

If the normal-light mode switch of a mode selector switch at the scope switch 29 is operated, for example, the light source unit 3A enters the state to sequentially supply illumination light in normal-light mode, that is, R, G and B lights, to the light guide fiber 9, and the processor 4A enters the state to execute signal processing corresponding to the normal-light mode.

If the fluorescent mode switch of a mode selector switch is operated, the light source unit 3A enters a state to sequentially supply the illumination light in the fluorescent mode, that is, R1, G1 and E1 lights, to the light guide fiber 9, and the processor 4A enters the state to execute signal processing corresponding to the fluorescent mode.

The CCD 28 is driven by a CCD drive signal from a CCD drive circuit 31 installed in the processor 4A, performs photoelectric conversion for the optical image formed in the CCD 28, and outputs the image signals.

The image signals are amplified by a preamplifier 32 installed in the processor 4A, then are amplified up to a predetermined level by an auto-gain control (AGC) circuit 33, converted from analog signals to digital signals (image data) by an A/D conversion circuit 34, and each image data is temporarily stored in a first frame memory 36a, second frame memory 36b, and third frame memory 36c via a multiplexer 35 which performs switching.

The CCD drive circuit 31 is controlled by the control circuit 37. Concretely, in the normal-light mode, as described later, the light quantity to be received by the CCD 28 decreases more when illumination is performed with the B filter 21c than when illumination is performed with the other filters R or G 21a or 21b, thus activating the electronic shutter function.

In the fluorescent mode as well, the light quantity to be received by the CCD 28 during the period of obtaining fluorescent images by irradiating the excitation light using the E1 filter 22c is much lower than the case of the reflected light of which illumination is performed using the R1 or G1 filter 22a or 22b, thus activating the electronic shutter function.

The control circuit 37 controls the motor for moving 20 according to the selected mode. The motor for rotation 16 is controlled by the control circuit 37, and the output of the encoder (not shown), mounted on the rotation axis of the motor for rotation 16, is input to the control circuit 37, and the control circuit 37 controls the CCD drive circuit 31 and the switching of the multiplexer 35, synchronizing with the output of the encoder.

The control circuit 37 controls the switching of the multiplexer 35, where in normal-light mode each image data captured under the illumination of the R, G and B filters 21a, 21b and 21c is sequentially stored in the first frame memory 36a, second frame memory 36b, and third frame memory 36c respectively.

In fluorescent mode as well, the control circuit 37 controls the switching of the multiplexer 35, where each signal captured under the illumination of the R1, G1 and E1 filters 22a, 22b and 22c is sequentially stored in the first frame memory 36a, second frame memory 36b, and third frame memory 36c respectively.

The image data stored in the frame memories 36a to 36c are input to an image processing circuit 38, where, as described later with reference to FIG. 4, image processing is performed on the input signals so as to convert the input signals into the output signals having hue which allows easily identifying normal tissue and pathologically affected tissue using the matrix circuit 34, then the image data is converted into analog RGB signals using a D/A conversion circuit 39, and is output to the monitor 5.

In the image processing circuit 38, which is one of the characteristics of the present embodiment, three signals to be input into this image processing circuit 38, that is, the reflected light image capturing signals generated by capturing the image of reflected light in the biological tissue using two illumination lights G1 and R1 in the narrow band, and the fluorescent image signal generated by capturing the image of fluorescence which is generated in the biological tissue by the excitation light E1, are matrix-converted by the image processing circuit 38, and are allocated to three channels, R, G and B, for color display.

In this processor 4A, a light adjustment circuit 40 is installed so as to automatically control the opening amount of the light source aperture 13 in the light source unit 3A based on the signal passing through the preamplifier 32. This light adjustment circuit 40 is controlled by the control circuit 37.

The control circuit 37 controls the lamp current which drives the lamp 12 of the lamp drive circuit 11 for light emission.

This control circuit 37 also performs the control operation according to an operation of the scope switch 29.

The electronic endoscope 2A has a scope ID generation section 41 for generating unique ID information which includes at least a model information of the electronic endoscope 2A, and when the electronic endoscope 2A is connected to the processor 4A, the model information of the connected electronic endoscope 2A is detected by a model detection circuit 42 installed at the processor 4A side, and the model information is sent to the control circuit 37.

The control circuit 37 sends control signals for setting the parameters of the matrix circuit of the image processing circuit 38 to be appropriate values according to the characteristics of the model of the connected electronic endoscope 2A. A setting switch 43 for selecting and setting the parameters of the matrix circuit is also connected to the image processing circuit 38.

A concrete configuration of the image processing circuit 38 will be described with reference to FIG. 4.

Figure 4:
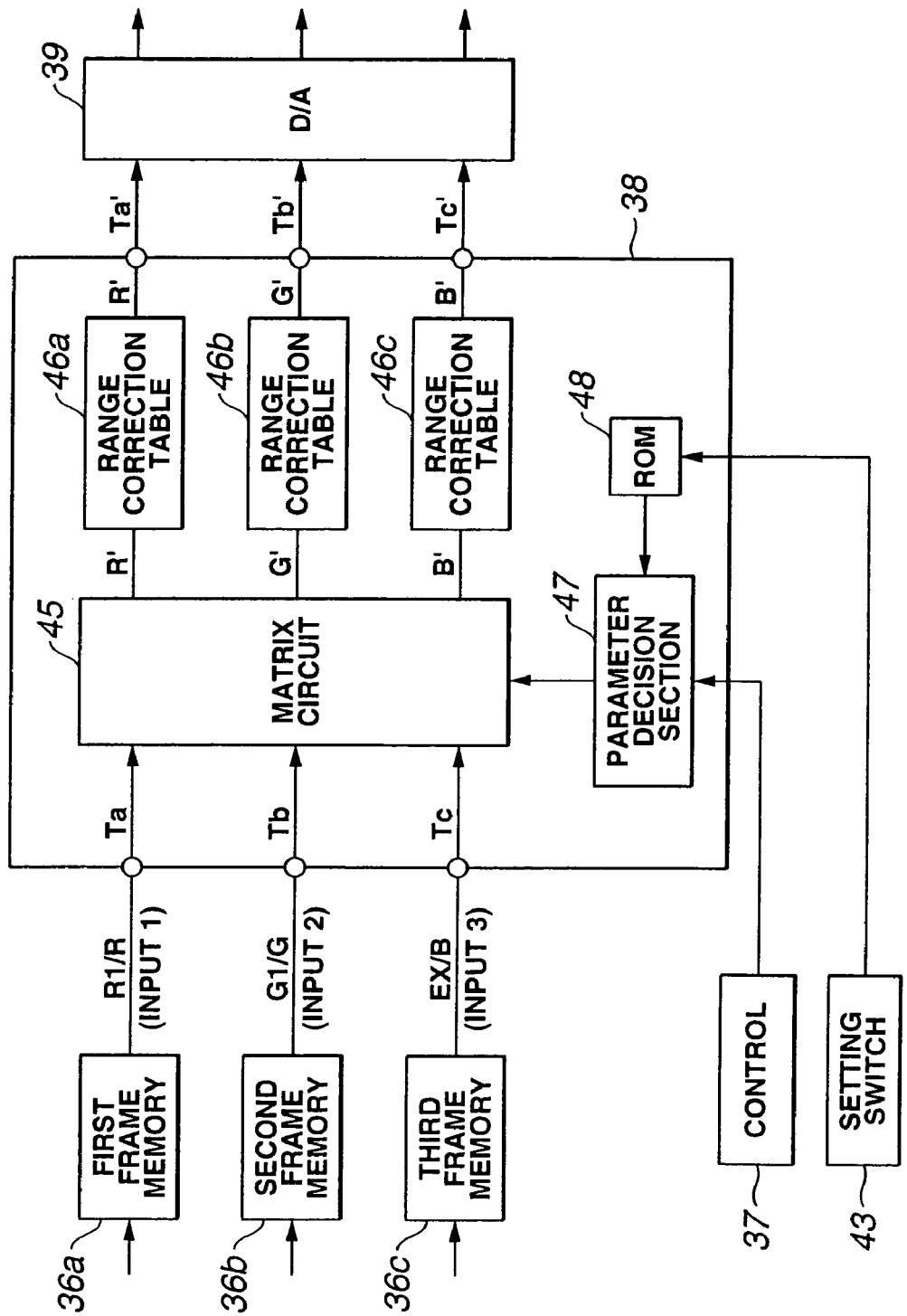

As FIG. 4 shows, R, G and B signals are input from the first to the third frame memories 36a to 36c to the three input ends Ta, Tb and Tc of the image processing circuit 38 in the normal-light image mode, and signals R1, G1 and EX are input in the fluorescent image mode. Here for simplification, signals R1 and G1 show image capturing signals generated by capturing the reflection signals in biological tissue under the illumination lights R1 and G1, and signal EX shows the signal of a fluorescent image captured under the excitation light E1.

The signals R, G and B, or signals R1, G1 and EX, which are input to the input ends Ta, Tb and Tc, are converted into the signals R', G' and B' by the matrix circuit 45, and are output. Actually in the normal-light image mode, the input signals R, G and B are output as is. In the fluorescent image mode, on the other hand, the input signals R1, G1 and EX are converted into the signals R', G' and B', and are output.

In other words, if the three rows and the three columns of matrix elements (also called parameters) of a matrix circuit 45 is aij, then R', G' and B' is given by $$\begin{bmatrix} R' \\ G' \\ B' \end{bmatrix} = \begin{bmatrix} a_{11} & a_{12} & a_{13} \\ a_{21} & a_{22} & a_{23} \\ a_{31} & a_{32} & a_{33} \end{bmatrix} \begin{bmatrix} R1 \\ G1 \\ EX \end{bmatrix} \quad \text{Formula 1}$$

$$\begin{bmatrix} R' \\ G' \\ B' \end{bmatrix} = \begin{bmatrix} a_{11} & a_{12} & a_{13} \\ a_{21} & a_{22} & a_{23} \\ a_{31} & a_{32} & a_{33} \end{bmatrix} \begin{bmatrix} \text{Input 1} \\ \text{Input 2} \\ \text{Input 3} \end{bmatrix} \quad \text{Formula 1'}$$

Formula 1 shows the case of the fluorescent image mode. Formula 1', on the other hand, shows the case when the more general input signals, that is, inputs 1, 2 and 3 (the inputs 1, 2 and 3 are signals R, G and B in the normal-light mode, and R1, G1 and EX in fluorescent mode), are converted into the signals R', G' and B' by the matrix circuit 45, and are output.

If the signals exceed a predetermined range, the output signals R', G' and B' of the matrix circuit 45 are further corrected using the three range correction tables 46a, 46b and 46c, then the result becomes the output signals R', G' and B' of the image processing circuit 38, and are output from the output ends Ta', Tb' and Tc' (connected to the R, G and B channels of the monitor 5) to the D/A conversion circuit 39.

The range correction tables 46a, 46b and 46c are for correcting the abnormal values of the signals to be input to these range correction tables 46a, 46b and 46c, and the signals having a normal signal level are output as is, so for simplification, the output signals of the range correction tables 46a, 46b and 46c are also shown as R', G' and B'.

This matrix circuit 45 is connected to a parameter decision section 47 for deciding the parameter aij thereof, and the control circuit 37 and a ROM 48 are connected to this parameter decision section 47. And a setting switch 43 is connected to this ROM 48.

In the ROM 48, a plurality of matrix elements having a different parameter aij are stored, and a parameter, decided (selected) by the parameter decision section 47, using the control signals from the control circuit 37, is sent to the matrix circuit 45, and the parameter aij in the Formula 1' is decided.

Concretely, a control signal for setting a parameter suitable for the model of the endoscope 2A connected to the processor 4A is sent to the parameter decision section 47 by the control circuit 37, and the parameter decision section 47 decides the parameter corresponding to the control signal.

If the user selects and sets a parameter stored in the ROM 48 by operating the setting switch 43, then the parameter decision section 47 sets the parameter of the matrix circuit 45 to be the selected.

According to the present embodiment, the endoscope system 1A is characterized in that the filter characteristic of the RGB filter 21 and the filter for fluorescent observation 22 of the switching filter 17 of the light source unit 3A, and the excitation light cut filter 27 installed in the image capturing optical path of the electronic endoscope 2A, are set as shown in FIG. 3A to FIG. 3C, so that the degree of separation between the normal tissue and the pathologically affected tissue can be increased.

The present embodiment is also characterized in that matrix conversion is performed especially on the input signals R1, G1 and EX using the image processing circuit 38, so that the hue is different between the normal tissue and the pathologically affected tissue, and the images of the pathologically affected tissue are displayed in a predetermined hue to make identification easier.

At first an increase of ability of distinction will be described with reference to FIG. 5 and other drawings.

Figure 5A:
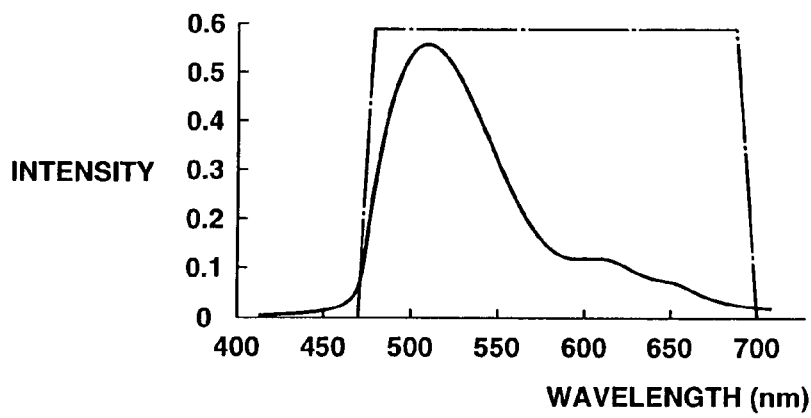
FIG. 5A and FIG. 5B are diagrams depicting intensity distribution characteristic examples with respect to the wavelength of fluorescent images and reflected light images for biological tissue.
Figure 5B:
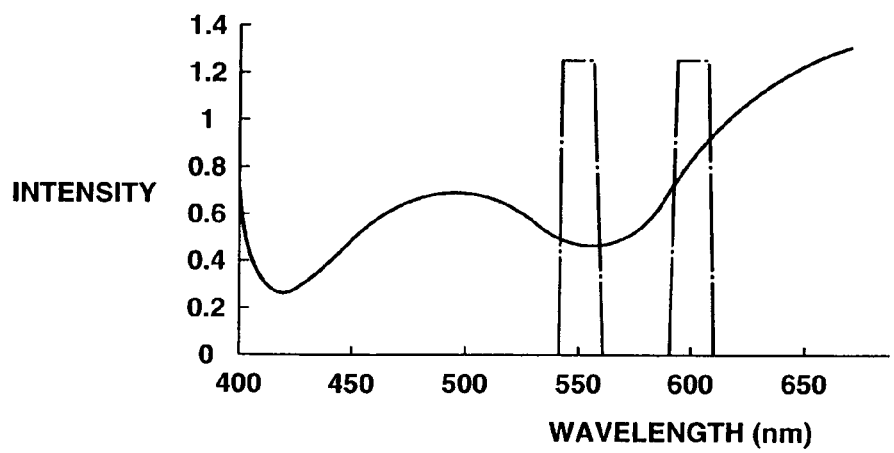

FIG. 5A shows an intensity distribution characteristic example with respect to the wavelength of the fluorescent image obtained from biological tissue, and FIG. 5B shows an intensity distribution characteristic example with respect to the wavelength of reflected light obtained from biological tissue.

FIG. 5A shows the distribution characteristic which peaks at around 520 nm, and in the present embodiment, the transmission characteristic by the excitation light cut filter 27 is set to include a wavelength band around 520 nm.

In the intensity characteristic of the reflected light in FIG. 5B, absorption by hemoglobin is high at around 550 nm, and reflection intensity drops at around this wavelength. The wavelength around 600 nm is a zone where no absorption by hemoglobin occurs.

The center wavelength of the two filters 22a and 22b (G1 and R1 in FIG. 3B) are set to 550 nm and 600 nm.

In other words, in the present embodiment, the band of the R1 filter 22a is set to an area where the absorptivity of oxidized hemoglobin is low, and the band of the G1 filter 22b is set to an area where the absorptivity of oxidized hemoglobin is high.

For the lights G1 and R1 which are the first and second illumination lights (reflected lights) when the biological tissue is illuminated in the fluorescent mode and is captured by the reflected light thereof, the wavelength width is set to 20 nm, for example (this may be set to 20 nm or less, as described later).

The transmittance of the light in the blue area (long wavelength area) shielded by the E1 filter 22c and in the blue area (short wavelength area) shielded by the excitation light cut filter 27 are set to OD4 (1/10000) or less.

Now the reason why the wavelength (central wavelength) is set to 550 nm and 600 nm when an image is obtained by the two reflected lights in the fluorescent mode, as described above, will be described with reference to FIG. 6 and other drawings. The wavelength band width of the fluorescent image is smaller with respect to the intensity of images generated by the reflected light, and the luminance level thereof becomes relatively low compared with the images generated by the reflected light, which makes identification by hue difficult, so a wide band including at least the peak wavelength (around 520 nm) in the fluorescent spectrum is set so as to increase the luminance level, making identification by hue easier.

Figure 6:
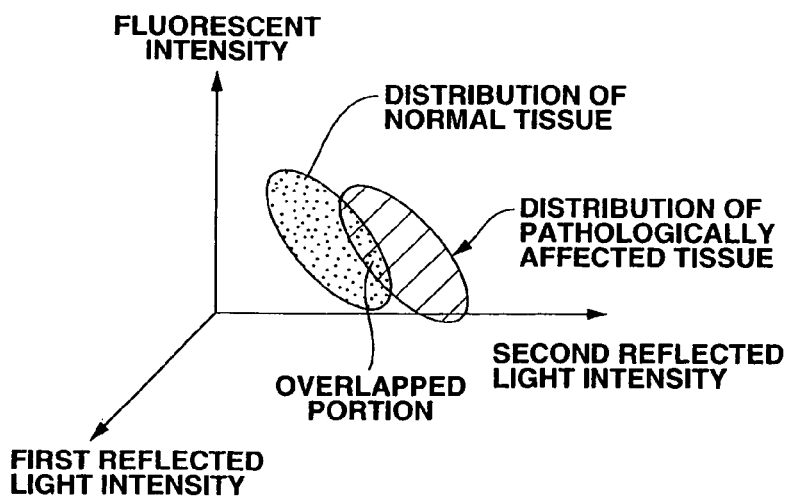

FIG. 6 shows the distribution of the normal sections and the pathologically affected sections which are plotted on spatial coordinates, where three axes are the two reflected light intensities and the fluorescent intensity. In FIG. 6, the dotted section shows normal tissue in the biological tissue, and the diagonal line section shows the pathologically affected tissue in the biological tissue.

As the section where the normal tissue and the pathologically affected tissue overlap becomes smaller, it is easier to identify the normal tissue and the pathologically affected tissue, so in the present embodiment, the bands of the two reflected lights are calculated by a statistical method (specifically Fisher's discriminate function) so that the overlapped section becomes the minimum.

In other words, the ability of distinction S is determined by the overlap of the distribution of the normal tissue and the pathologically affected tissue using the following formula.

Ability of distinction $S=1-$(overlapped section of the normal tissue and the pathologically affected tissue)/(entire distribution)

And the acquired ability of distinction S is calculated changing the central wavelength of the first reflected light and the second reflected light.

Figure 7:
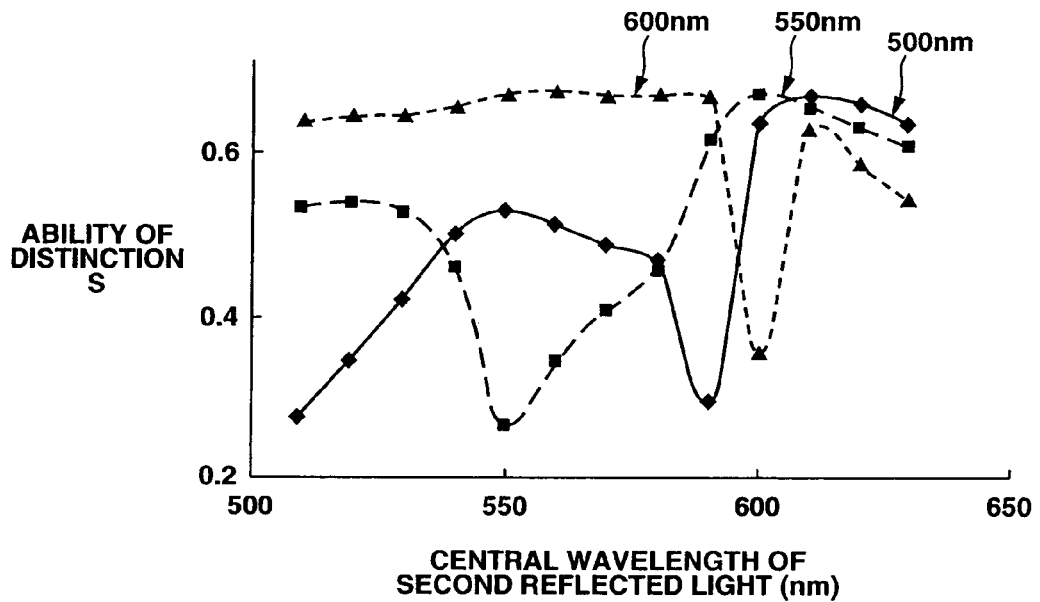

FIG. 7 shows ability of distinction S, which is acquired with respect to the central wavelength of the second reflected light when the first reflected light is changed as a parameter. Here the central wavelength of the first reflected light is changed to 510 nm, 550 nm and 600 nm as a parameter.

According to FIG. 7, the highest ability of distinction S is acquired when the central wavelength of the first reflected light is 550 nm and the central wavelength of the second reflected light is 600 nm. Also the highest ability of distinction S is acquired when the central wavelength of the first reflected light is 600 nm, and the central wavelength of the second reflected light is 550 nm if the central wavelength of the first reflected light and that of the second reflected light are switched.

Figure 8:
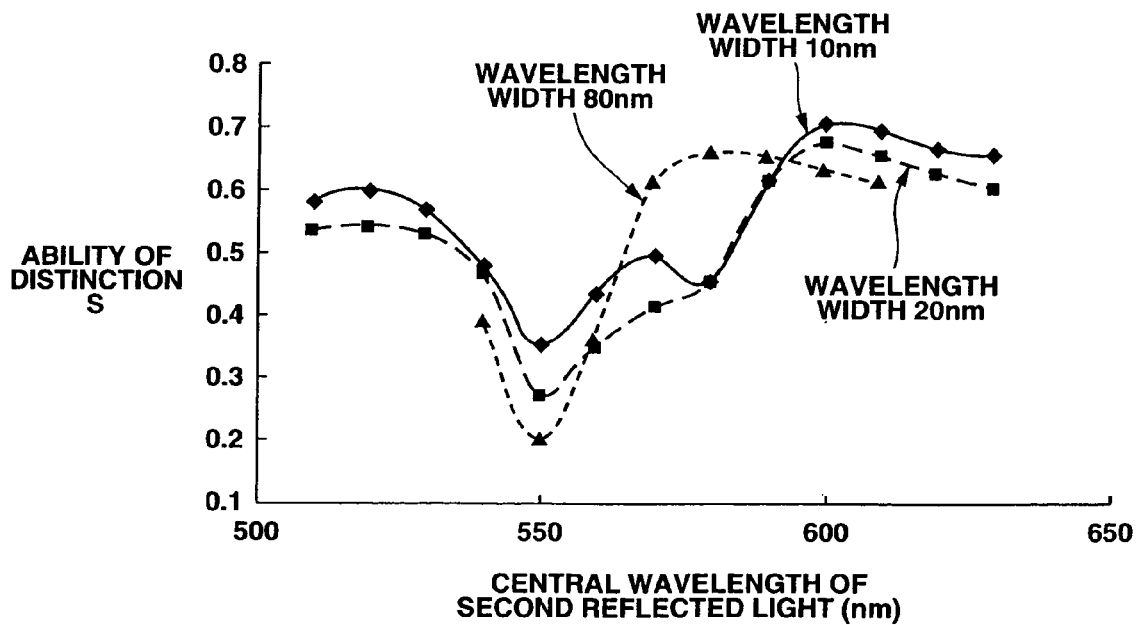

FIG. 8 shows ability of distinction S, which is acquired when the central wavelength of the first reflected light is 550 nm and the wavelength width thereof is changed as a parameter. In FIG. 8, the wavelength width is changed to 80 nm, 20 nm and 10 nm.

According to FIG. 8, when the central wavelength of the first reflected light is 550 nm, a high ability of distinction S is acquired when the wavelength width is about 20 nm or less. According to FIG. 8, a higher ability of distinction S is acquired when the wavelength width is 10 nm and not 20 nm, but as the wavelength width decreases, intensity decreases and the S/N drops. Therefore in the present embodiment, wavelength width is set to 20 nm. The wavelength width may be set to 20 nm or less, 10 nm for example, according to the S/N of the signal processing system of the processor 4A.

According to FIG. 7 and FIG. 8, the wavelength of the first and second reflected lights (illumination lights) are set to 550 nm and 600 nm respectively, and the wavelength width thereof is set to 20 nm, so that a high ability of distinction S can be acquired, that is, the normal tissue and the pathologically affected tissue can be distributed as separately as possible.

In the present embodiment, the intensity of the fluorescent image is much lower compared with the case of the reflected light, as mentioned above, and the excitation light cut filter 27 having a characteristic for obtaining fluorescent images, which includes a wavelength band around 520 nm where the intensity of the fluorescent image reaches a peak, as shown in FIG. 5A, is used. By this, a fluorescent image with good S/N can be obtained.

Also in the present embodiment, the parameters of the matrix conversion by the image processing circuit 38 are set to appropriate values so that hue (including luminance), allows easy identification of the normal tissue and the pathologically affected tissue on the display image.

Then the normal tissue and the pathologically affected tissue are displayed on the chromaticity diagrams shown in FIG. 9 to FIG. 12 in pseudo-colors in the luminance and hue states, so as to be easily identified.

Figure 13:
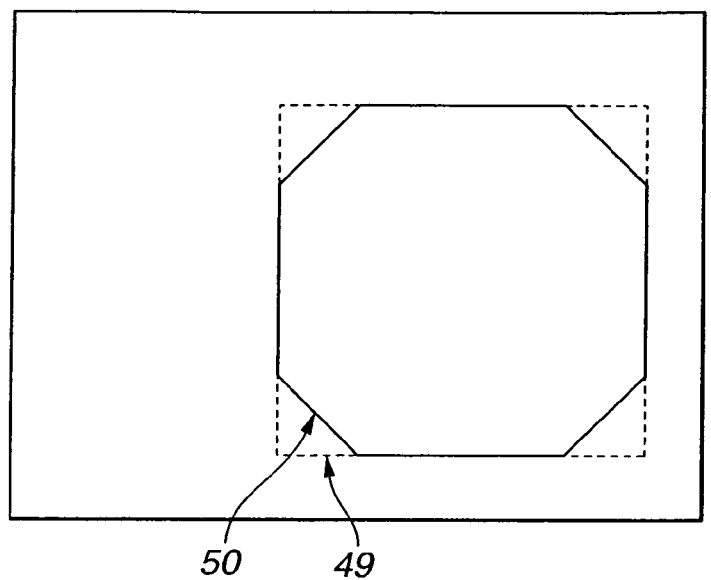

FIG. 13 shows the display screen of the monitor 5. On the monitor 5, the square section 49 in FIG. 13 is the area of image captured by the CCD 28, and the octagonal section, when the four corners of the square section 49 which become dark are cutoff, is the display area 50 of the endoscope image, and according to the present embodiment, the image processing circuit 38 is operated only during the image signal period corresponding to this range of the display area 50, so that the processing volume, such as matrix conversion, by the image processing circuit 38, can be decreased and high-speed processing can be implemented.

The functions of the present embodiment with such a configuration will now be described.

As FIG. 1 shows, the connector for the light source 10 of the electronic endoscope 2A is connected to the light source unit 3A, and the connector for signals, which is not shown, of the electronic endoscope 2A is connected to the processor 4A. And the endoscope system is set to the connection state as shown in FIG. 1, and the power supply of each unit is turned ON for operation. Then the control circuit 37 executes the initial setting operation, and sets the system to operate in normal-light mode, for example, in this initial setting state.

In this mode, the control circuit 37 controls the motor for moving 20 of the light source unit 3A, and sets the switching filter 17 so that the RGB filter 21 in the inner circle side to position in the illumination light path.

And the control circuit 37 rotates the rotation motor 16. The white light of the lamp 12 is filtered by the R, G and B filters 21a, 21b and 21c of the switching filter 17, which are sequentially positioned in the illumination light path, and is emitted as R, G and B illumination light to the observation target side.

In the normal-light mode, the illumination light (to the observation target side) by the switching filter 17 is generated by the R, G and B filters 21a, 21b and 21c, which are sequentially positioned in the illumination light path.

The signals captured by the CCD 28 during sequential illumination by the R, G and B lights are amplified and A/D converted, then are sequentially stored in the first frame memory 36a, second frame memory 36b, and third frame memory 36c by the multiplexer 35, which is sequentially switched by the control circuit 37.

The image data with R, G and B color components, which is stored in the frame memories 36a to 36c, is simultaneously read during a predetermined frame period (e.g. 33 ms, that is 1/30 sec.), and is input to the image processing circuit 38.

In the normal-light mode, the image processing circuit 38 outputs the input signals as is. For example, the input signals may be output to the D/A conversion circuit 39 after passing through the matrix circuit 45 and the range correction tables 46a to 46c, or may pass through the matrix circuit 45, which is set to normal-light mode.

In this case, the control circuit 37 sends the control signal for normal-light mode to the parameter decision section 47, and the parameter decision section 47 outputs the input signals R, G and B as output signals, setting the parameter aij of the matrix circuit 45 to "1" only for the diagonal elements of a11, a22 and a33, and to "0" for the rest. In this case, the range correction tables 46a to 46c pass the signals through, for example.

In this way, the captured signals are transformed into analog standard image signals, that is, RGB signals in this case via the D/A conversion circuit 39, and are output from the R, G and B channels to the monitor 5, and a normal-light observation image (where color tone is reflected when the subject is directly observed with irradiated white light) is displayed on the display screen of the monitor 5 in color.

As described above, concerning the quantity of reflected light at the subject side when the illumination is performed through the B filter 21c, the quantity of received light of the color B component image is less than the quantity of the received light of the R and G color component images, since the short wavelength side has been cut by the excitation light cut filter 27 when the CCD 28 receives the light, so in this state the white balance is lost.

To prevent this, the control % circuit 37 increases, doubles for example, the amplification factor of the CCD 28 when the image of an observation target is captured during an illumination period with the B filter 21c via the CCD drive circuit 31.

The control circuit 37 controls the lamp drive circuit 11, and increases the lamp current for driving the lamp 12 during the illumination period with the B filter 21c to larger than the value of normal-light lamp current, for example, so as to increase the quantity of the illumination light of B.

The control circuit 37 also controls the CCD drive circuit 31 and operates the functions of the electronic shutter of the CCD 28. In other words, the CCD 28 is driven such that the image capturing period becomes shorter during the illumination period of R and G with images being captured only during a part of the illumination period, and the image capturing period becomes longer during the illumination period of B with images being captured during the entire illumination period.

In this way, normal-light images with good white balance are displayed on the monitor 5. For setting the image capturing period by the electronic shutter, the concrete values of the image capturing period are stored in a memory, which is not shown, in the control circuit 37 in advance, so that when the image of a white subject is captured, the subject is displayed as white on the monitor 5 (or the image of the white subject may be captured during the initial setting after power is turned ON, and an image capturing period by the electronic shutter is concretely set). At this time, not the image capturing period of the electronic shutter but a value of the CCD amplification factor and a value of the lamp current may be stored, and these values may be used either alone or in combination.

In this way, a subject is observed in the normal-light mode, and when fluorescent observation is required for a target affected area of the subject, for example, the fluorescent mode switch of the mode selector switch of the scope switch 29 is operated.

Then the control circuit 37 receives this control signal and drives the motor for moving 20 of the light source unit 3A, and moves the switching filter 17 so that the filter for fluorescent observation 22 is set to be positioned on the illumination light path in order to switch to fluorescent mode.

When the fluorescent mode is set, the illumination light in the fluorescent mode, that is, the R1, G1 and E1 lights shown in FIG. 3B, are sequentially supplied to the light guide fiber 9 of the electronic endoscope 2A.

And the R1, G1 and E1 lights are sequentially irradiated onto the subject. In the case of the R1 and G1 illumination, operation is the same as the case when the R and G lights are sequentially irradiated in the normal-light mode. In other words, in this case the reflected light of R1 and G1 from the subject is received by the CCD 28. And in this case, the CCD 28 captures images without the influence of the excitation light cut filter 27.

Whereas when the excitation light E1 is irradiated, the reflected light of the excitation light E1 is almost completely shielded by the excitation light cut filter 27, and the CCD 28 receives fluorescence from the subject side in the transmission band of the excitation light cut filter 27.

The intensity of the fluorescence is much smaller than the intensity of the reflected light of R1 and G1 from the subject, so an operation similar to the above mentioned illumination of R and G in the normal-light mode, the illumination of B, and the signal processing of these cases are executed so that bright fluorescent images, for easy comparison with images of the reflected light of R1 and G1 from the subject, are displayed.

Concretely, when the reflected light of R1 and G1 from the subject is captured, the image data captured by the CCD 28 only during a part of the illumination period using the electronic shutter is stored in the first frame memory 36a and the second frame memory 36b.

Whereas when the excitation light of E1 is irradiated and the fluorescent image thereof is captured, the amplification factor of the CCD 28 is increased from 10 to 100 times, for example, the lamp current is also increased, and the quantity of the illumination light of the excitation light is also increased. And the fluorescent image data captured in this case is stored in the third frame memory 36c.

And the image data of the first frame memory 36a to the third frame memory 36c is read simultaneously in one frame period, and is input to the image processing circuit 38.

The image processing circuit 38 has the configuration shown in FIG. 4, and the input signals R1, G1 and EX are converted by the matrix circuit 45, and become the output signals R', G' and B'. In this case, this processing is influenced by the light transmission characteristic (especially with respect to wavelength) of the light guide 9 and the sensitivity characteristic (especially with respect to wavelength) of the built-in CCD 28 depending on the model of the electronic endoscope 2A to actually be used, even if the same light source unit 3A is used. Also the relative sizes of the input signals R1, G1 and EX change, since the light absorption and other characteristics differ depending on the subject to be observed, so the model in use and the influence of the subject are checked in advance, and the control circuit 37 sends the control signal to the parameter decision section 47, so as to cancel the dependency on the model and the subject.

Therefore the output signals R', G' and B', where the characteristics depending on the model and the subject have been compensated for, can be obtained from the matrix circuit 45. For example, when a different electronic endoscope model (referred to as 2C in this description) with a different transmission characteristic of the light guide 9 is used instead of the electronic endoscope 2A, and an image of the biological tissue is captured in a state which is the same as the electronic endoscope 2A, the values of the signals R1, G1 and EX to be input to the image processing circuit 38 are different from the case of the electronic endoscope 2A, but the parameters of the matrix circuit 45 are set (to be values different from the electronic endoscope 2A) such that the relative values of the output signals R', G' and B', which pass through the matrix circuit 45, become the same as the case of the electronic endoscope 2A.

In this way, the parameters of the matrix circuit 45 are automatically set to appropriate values by the detection signal, which detected the model of the electronic endoscope (including illumination means for guiding light and illuminating the subject, and image capturing means), and the output signals R', G' and B', which do not depend on the model and the subject, are obtained from the matrix circuit 45.

When these output signals R', G' and B' deviate from the appropriate range, that is, the output signal values become too large or too small after the matrix conversion, the output signals are cut at the upper limit value and the lower limit value, and are corrected to the signal levels in the appropriate range by the range correction tables 46a to 46c (concretely, correction is executed such that the luminance level does not become less than "0" nor becomes "255" or more).

The signals which pass through the range correction tables 46a to 46c are converted to analog RGB signals by the D/A conversion circuit 39, and are displayed in pseudo-colors on the monitor 5.

According to the present embodiment, when the fluorescent mode is set, the matrix of the matrix circuit 45 is set to a matrix with values shown in the following Formulas 2 or 3 in the case of the standard model electronic endoscope 2A. Also the matrix of formula 4 or 5 can be set by a selection operation. The formulas 2 to 4 correspond to the chromaticity diagrams in FIG. 9 to FIG. 12 respectively.

$$\begin{bmatrix} a_{11} & a_{12} & a_{13} \\ a_{21} & a_{22} & a_{23} \\ a_{31} & a_{32} & a_{33} \end{bmatrix} = \begin{bmatrix} 1 & 0 & 0 \\ 0 & 0 & 1 \\ 0 & 1 & 0 \end{bmatrix} \quad \text{Formula 2}$$

$$\begin{bmatrix} a_{11} & a_{12} & a_{13} \\ a_{21} & a_{22} & a_{23} \\ a_{31} & a_{32} & a_{33} \end{bmatrix} = \begin{bmatrix} 0 & 1 & 0 \\ 0 & 0 & 1 \\ 1 & 0 & 0 \end{bmatrix} \quad \text{Formula 3}$$

$$\begin{bmatrix} a_{11} & a_{12} & a_{13} \\ a_{21} & a_{22} & a_{23} \\ a_{31} & a_{32} & a_{33} \end{bmatrix} = \begin{bmatrix} 0 & 1 & 0 \\ 1 & 0 & 0 \\ 0 & 0 & 1 \end{bmatrix} \quad \text{Formula 4}$$

$$\begin{bmatrix} a_{11} & a_{12} & a_{13} \\ a_{21} & a_{22} & a_{23} \\ a_{31} & a_{32} & a_{33} \end{bmatrix} = \begin{bmatrix} 1 & 0 & 0 \\ 0 & 1 & 0 \\ 0 & 0 & 1 \end{bmatrix} \quad \text{Formula 5}$$

Figure 9:
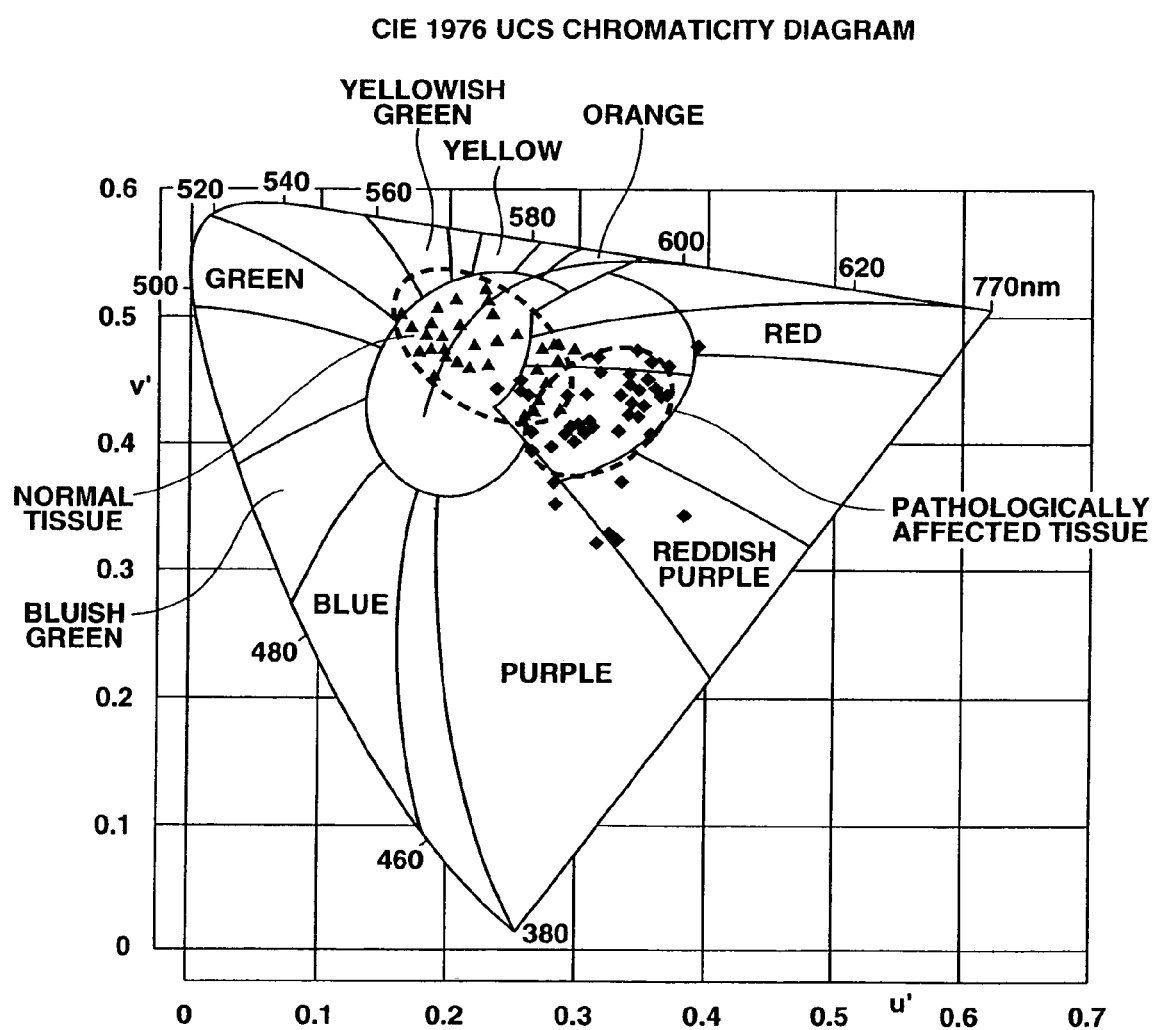
Figure 10:
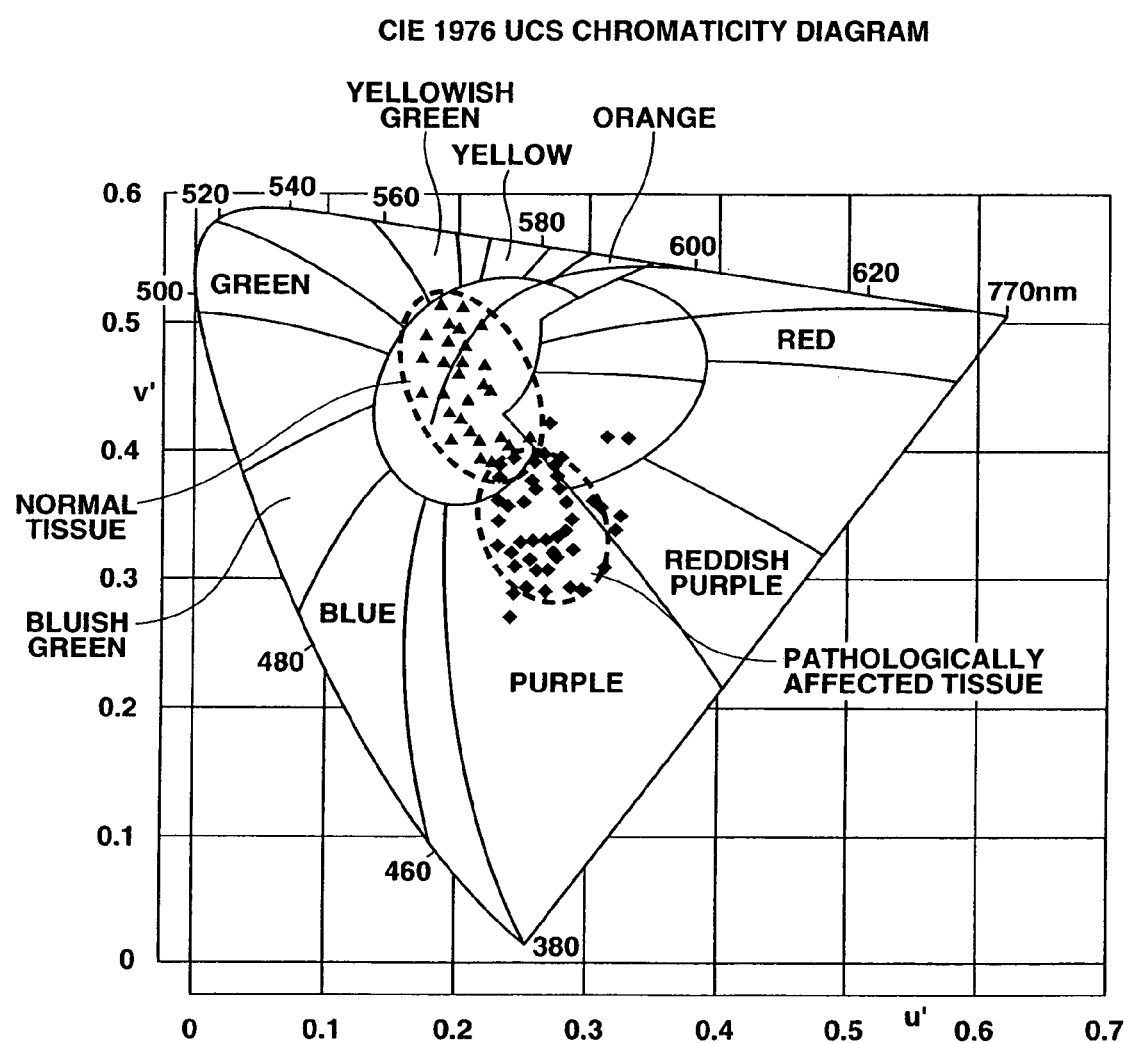

When the fluorescent mode is set, the matrix of the matrix circuit 45 is set according to the Formula 2 or 3, and in this case, in a state corresponding to the chromaticity diagram, the normal tissue section and the pathologically affected section are different, as shown in FIG. 9 or FIG. 10, and are displayed on the monitor 5 in pseudo-colors such that the pathologically affected tissue section enters roughly a single hue area.

In the case of the Formula 2, for example, the image signal EX in the fluorescent wavelength band is set at the G channel; one of the two reflected light wavelength bands, which has different central wavelengths and wavelength widths, is set at the R channel; and the other reflected light wavelength band is set at the B channel.

In the case of FIG. 9 which corresponds to Formula 2, the pathologically affected tissue section is limited to the area around the pink hue.

In the case of the Formula 3, the image signal EX in the fluorescent wavelength band is set at the G channel, just like the case of the Formula 2, and the remaining two signals in different reflected light wavelength bands are exchanged compared with the case of the Formula 2.

In the case of FIG. 10 which corresponds to Formula 3, the pathologically affected tissue section is limited to the area around purple hue. The display mode corresponding to FIG. 9 or FIG. 10 can be inter-switched by operating the switching mode in the fluorescent mode. And the user can display their choice.

Therefore an operator can judge it highly probable that the tissue is pathologically affected viewing from the section displayed in pink hue in the case of FIG. 9.

In the case of FIG. 10, an operator can judge it highly probable that the tissue is pathologically affected viewing from the section displayed in purple hue.

When it is judged as highly probable that the tissue is a pathologically affected viewing from the display state with pseudo-colors corresponding to the state of the chromaticity diagram in FIG. 9 or FIG. 10, and when the switch used at the mode for the pathologically affected tissue is provided further in the fluorescent mode of the scope switch 29 and is operated, the parameter decision section 47 changes further the parameters of the matrix circuit 45 by the control circuit 37 in order to set to the Formula 4 or Formula 5.

Figure 11:
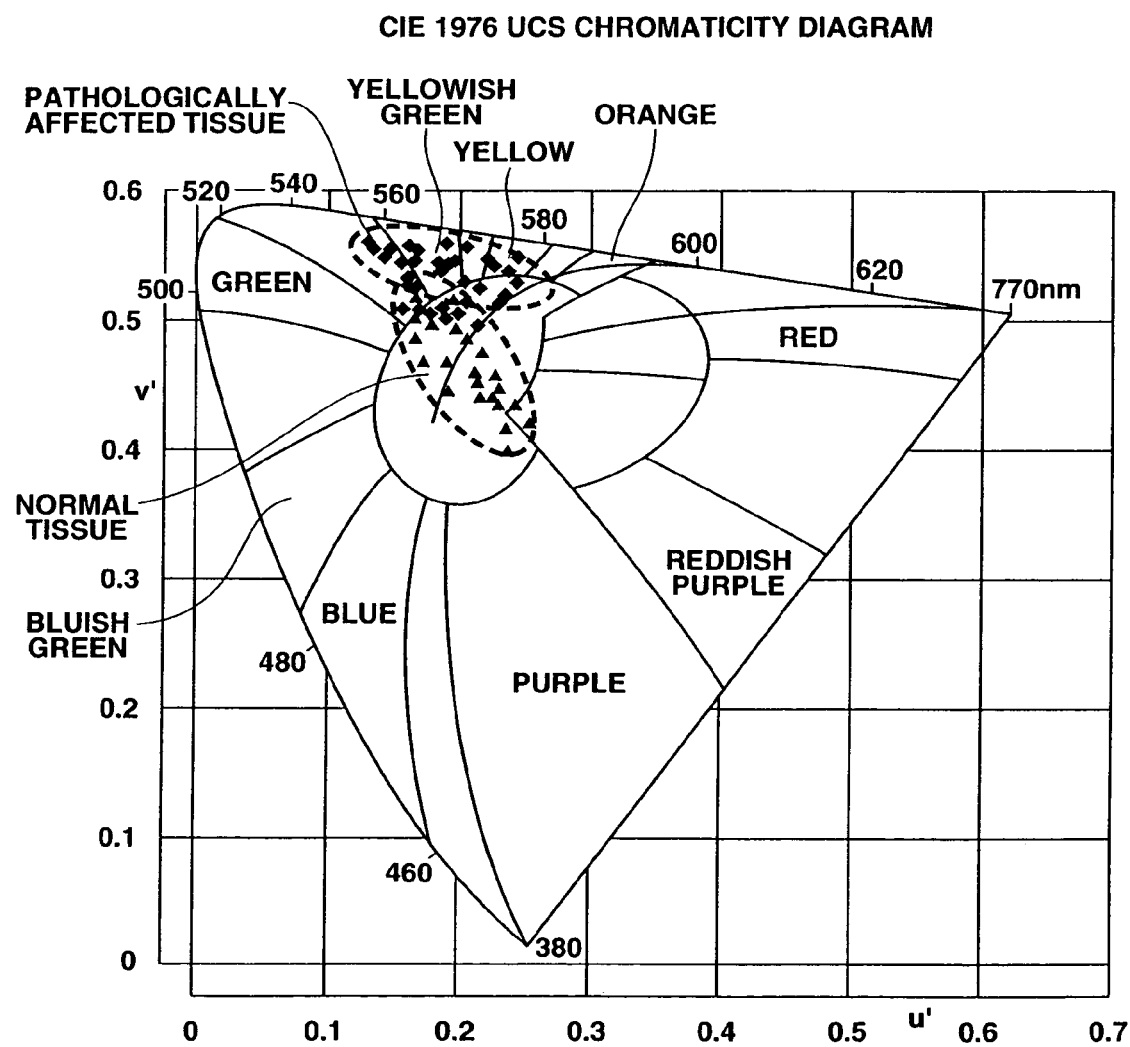
Figure 12:
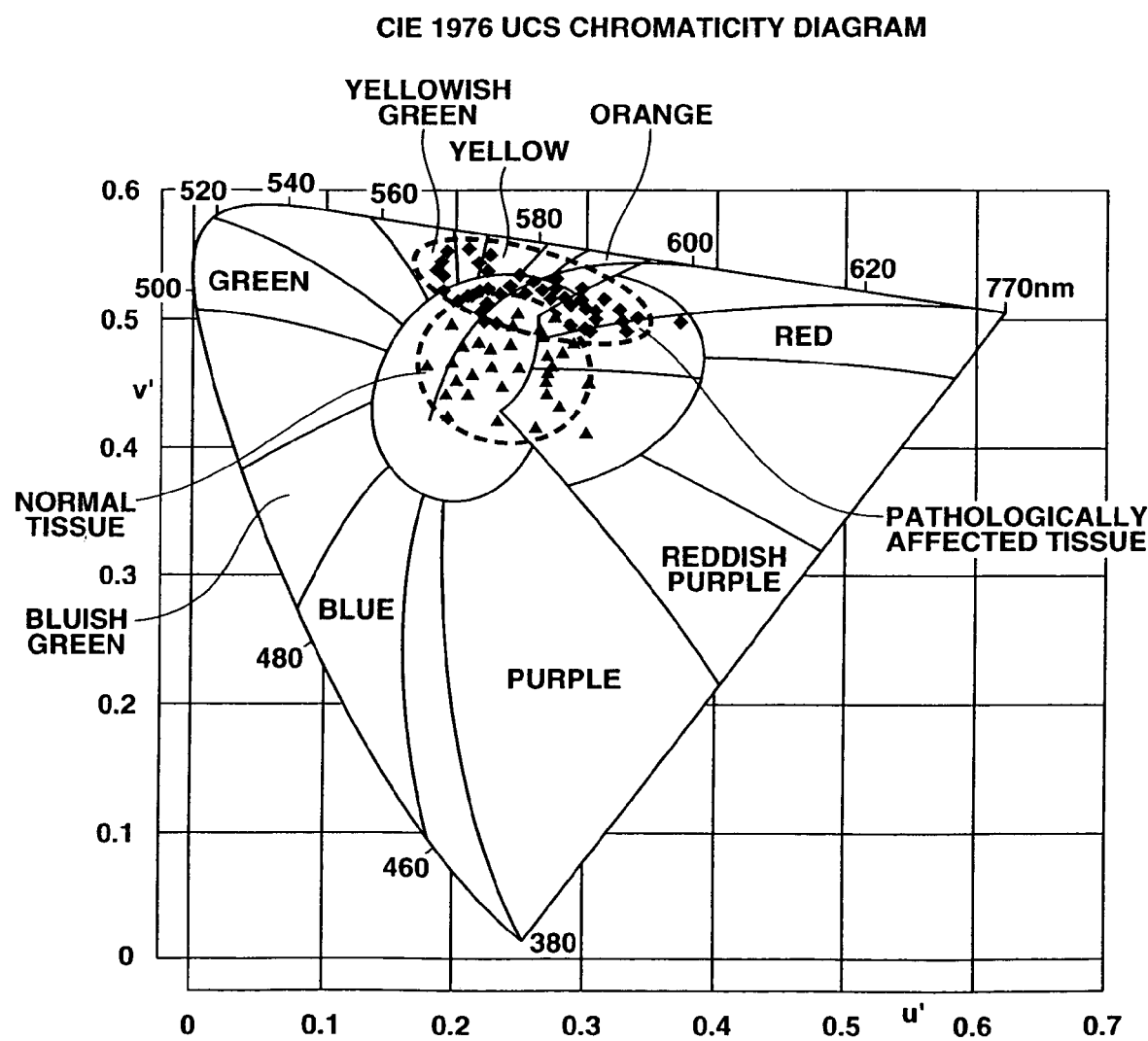

For the Formula 4 or the Formula 5, images in the fluorescent mode, that is, two reflected light images and a fluorescent image, are displayed in pseudo-colors in a state corresponding to the chromaticity diagram shown in FIG. 11 or FIG. 12.

In the Formula 4 or the Formula 5, the signal EX of the fluorescent image is set at the B channel, and the signals G and R1 of the two reflected light images are set at the G and R channels, or at the R and G channels respectively.

In the FIG. 11 or FIG. 12, the pathologically affected tissue is displayed with a plurality of hues, so it may not be appropriate to diagnose the normal tissue and the pathologically affected tissue at this point, but when it is judged as highly probable that the tissue is pathologically affected tissue as in FIG. 9 or FIG. 10, setting the display mode shown in FIG. 11 or FIG. 12 makes it easier to diagnose the state of the pathologically affected tissue in more detail due to the difference of hues. For example, the change of hues makes it easier to judge the degree of progress of the given pathological problem.

Therefore, according to the present embodiment, when two reflected light images and a fluorescent image are displayed in pseudo-colors, the wavelength of the reflected light images is set to an appropriate value so that the overlap of the normal tissue and the pathologically affected tissue sections is decreased and ability of distinction S is increased, and the wavelength of the fluorescent image is set such that the S/N thereof is high for easy identification, where the pathologically affected tissue is displayed in pseudo-colors so as to enter a single hue area, which is different from the normal tissue, and makes it easier to identify the pathologically affected tissue from the normal tissue, so an operator can easily diagnose the pathologically affected tissue. In other words, the present embodiment can provide an environment which makes diagnosis easier.

The excitation light cut filter 27, which is installed in front of the image pickup device of the electronic endoscope 2A, cuts the excitation light which includes a part of the blue wavelength band, and also the excitation light cut filter 27 transmits light in a visible region excluding a part of the blue light (transmits a part of the blue light and the entire region of the green and red wavelength band), for normal-light observation, therefore, capturing normal-light images and fluorescent images, and the display of normal-light images and fluorescent images by signal processing are possible by installing one image pickup device in the tip 8 of the insertion section 7.

Therefore, (compared with the case of housing a plurality of image pickup devices), the diameter of the insertion section 7 of the electronic endoscope 2A can be decreased, the application range where the electronic endoscope 2A can be inserted and used can be increased, and the pain caused to a patient at insertion can be decreased. An operator can insert the electronic endoscope 2A into a body cavity easily. Also cost can be decreased, since only one image pickup device is used.

Since blue, out of the entire visible light wavelength band (region), is used as the excitation light, a halogen lamp or a Xenon lamp, which can be used for normal-light illumination (white illumination), can be used for the lamp 12 of the light source unit 3A. Also, compared with the case when ultra-violet is used for the excitation light, transmission loss due to the light guide fiber 9 can be decreased, and the components for normal-light illumination can be used, which are merits.

In particular, the present embodiment can implement the endoscope system 1A which can display images (fluorescent images and reflected light images) in pseudo-colors for easy identification of normal tissue and pathologically affected tissue by a simple configuration.

Now a variant form of the first embodiment will be described.

Figure 14:
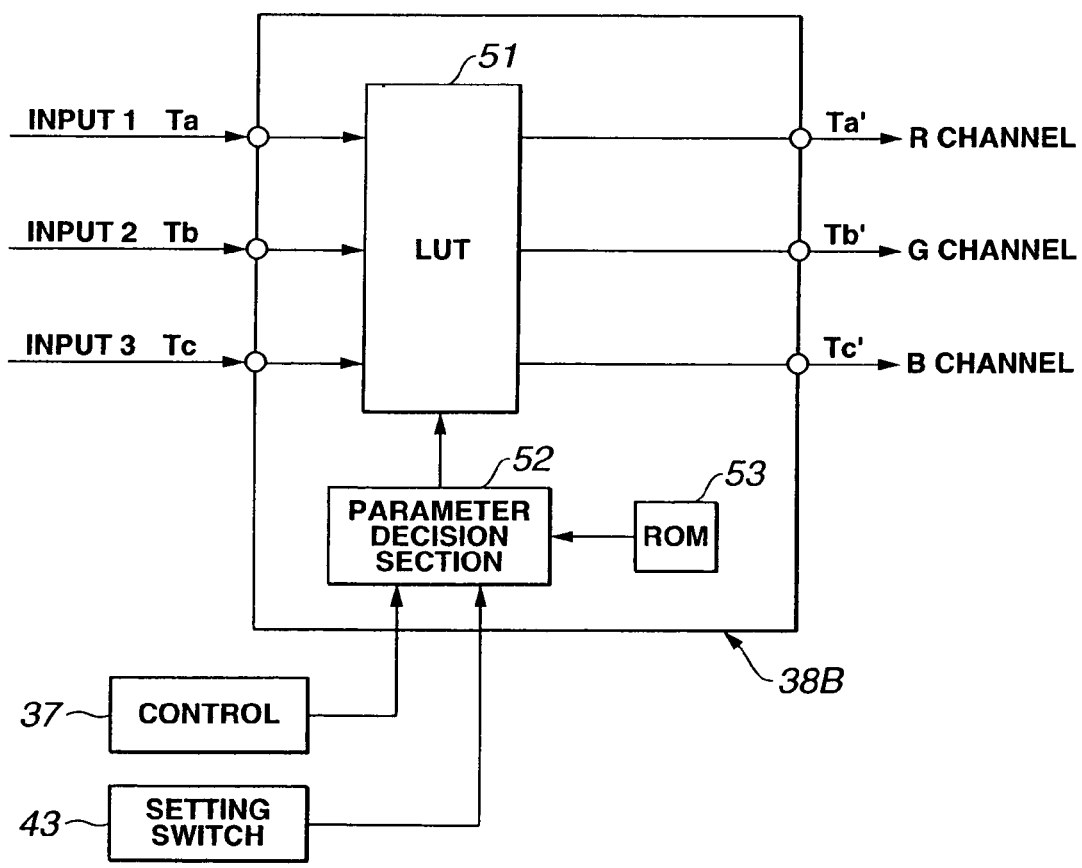

FIG. 14 shows a configuration of an image processing circuit 38B of a first variant form. The image processing circuit 38B of the first variant form uses a lookup table 51 (LUT in FIG. 4) instead of the matrix circuit 45 and level correction tables 46a to 46b in FIG. 4.

This lookup table 51 is connected to a ROM 53 via a parameter decision section 52, and the parameter decision section 47 is connected to the control circuit 37 and the setting switch 43.

In the ROM 53, a plurality of sets of output values are stored in advance, and the output values decided by the control signal of the control circuit 37 and the setting of the setting switch 43 via the parameter decision section 52 are set at the lookup table 51.

And for the three signals which are input from the input ends Ta to Tc, the corresponding output values are read from the lookup table 51, and are output from the output ends Ta', Tb' and Tc' to the R, G and B channels.

In the case of the normal-light mode, the lookup table 51 is set such that the input signals are output as is.

This variant form has functions and effects similar to the first embodiment.

Figure 15:
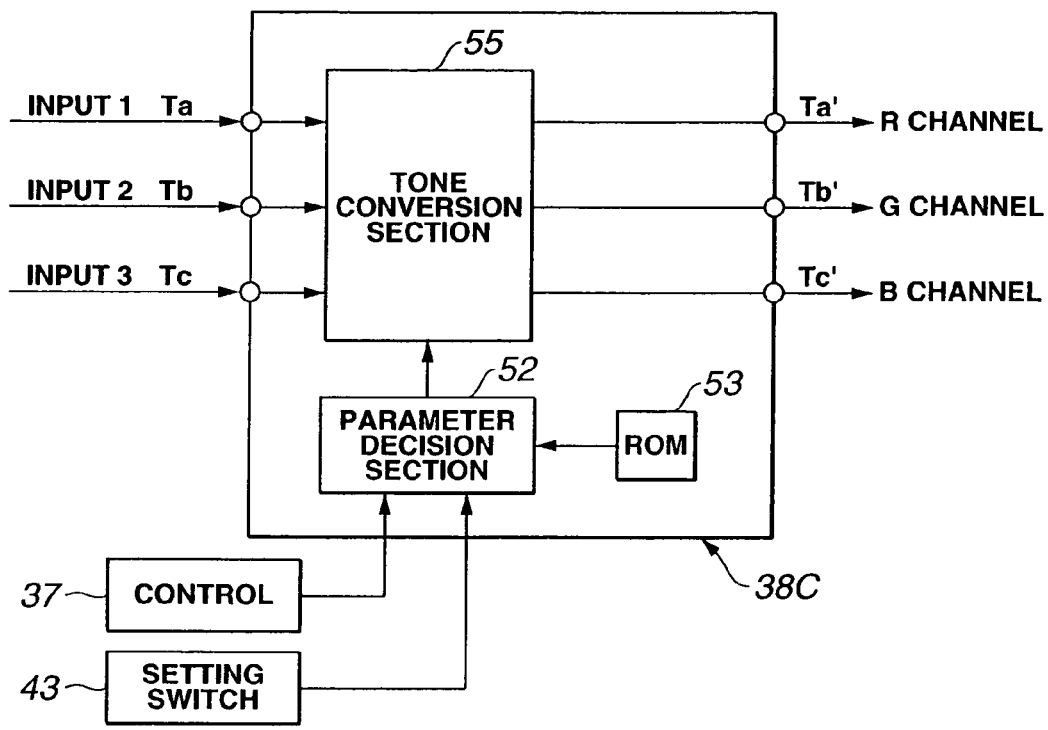

FIG. 15 shows an image processing circuit 38C of the second variant form.

This image processing circuit 38C has a color tone conversion section 55 instead of the lookup table 51 in FIG. 14.

The color tone conversion section 55 is comprised of a CPU and an arithmetic circuit, and performs the arithmetic processing of the matrix conversion of Formula 1' (and range correction table processing).

In the normal-light mode, the color tone conversion section 54 outputs the input signals as is (without executing arithmetic processing). This variant form has functions and effects similar to the first embodiment.

As described above, the present embodiment is an endoscope system, comprising a light source for illuminating the illumination light for two different wavelength bands and the excitation light for exciting fluorescence; image capturing means for capturing two reflected light images by reflected light when the illumination light is irradiated onto a biological tissue and is reflected, and a fluorescent image by fluorescence excited by the excitation light; image processing means for processing the two reflected light images and a fluorescent image and creating a processed image, and display means for displaying the processed image; wherein when the processed image is distributed on spatial coordinates where three axes are the intensities of the two different reflected lights and the fluorescence from the biological tissue, the wavelengths of the reflected lights and the fluorescence are selected such that the normal tissue and the pathologically affected tissue are separated on the three axes on the spatial coordinates, and the above mentioned image processing means further comprises means of inputting the three signals of the fluorescent image and the two reflected light images, and axial conversion means for operating the signals and converting them into signals comprised of three color components so that luminance and/or hue differ between the normal tissue and the pathologically affected tissue, and the images of the pathologically affected tissue enter within a specific range of hue, so as to obtain images which make it easier to identify the normal tissue and the pathologically affected tissue.

Second Embodiment

The second embodiment of the present invention will now be described with reference to FIG. 16. The configuration of the present embodiment is the same as the first embodiment, wherein a part of the characteristics of the excitation light cut filter 27, shown in FIG. 3C, has been changed.

Figure 16:
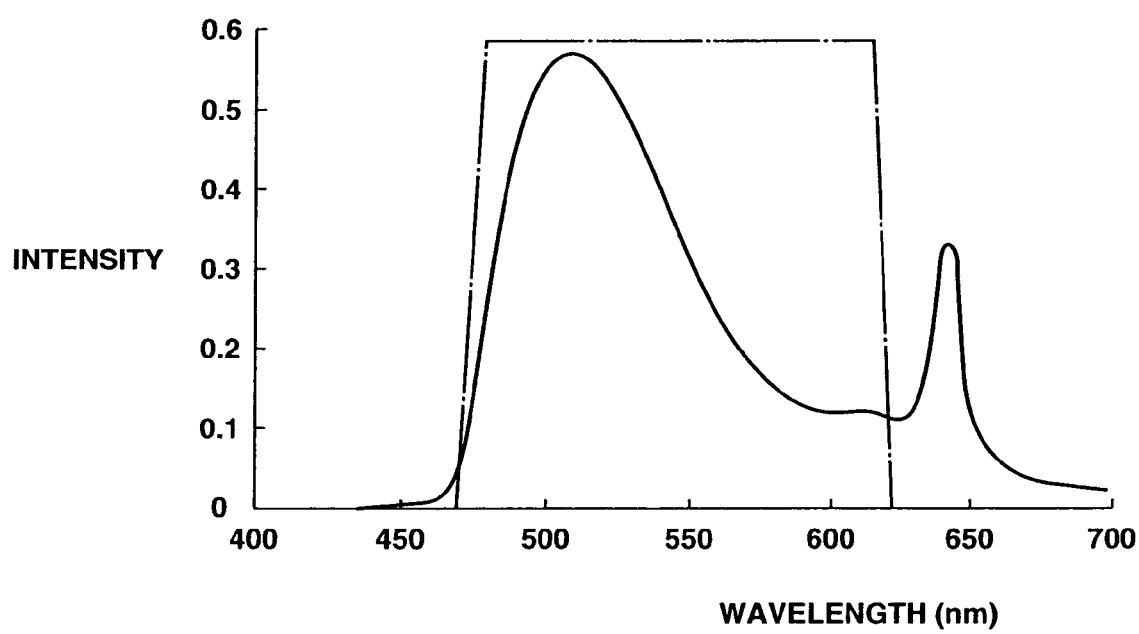
FIG. 16 is a diagram depicting the transmission characteristic of the excitation light cut filter in the second embodiment of the present invention.

FIG. 16 shows the characteristics of the intensity with respect to the wavelength of fluorescence obtained from a biological tissue which includes porphyrin. As FIG. 16 shows, when the biological tissue includes porphyrin, a wavelength band slightly longer than 620 nm may have a peak, which emits fluorescence due to porphyrin.

According to the present embodiment, to eliminate this influence of fluorescence generated by porphyrin, the longer wavelength side of the transmission characteristic of the excitation light cut filter 27 is cut at 620 nm, as indicated by the one-dotted line in FIG. 16, so that fluorescence at a wavelength longer than this wavelength is not received by the CCD.

In other words, the excitation light cut filter 27 is set such that the fluorescence from 470 nm, which are the same as the first embodiment, to 620 nm at the longer wavelength side, is transmitted, for example. The rest is the same as the first embodiment.

According to the present embodiment, in addition to the functions and effects of the first embodiment, the endoscope system can display the normal tissue and the pathologically affected tissue in pseudo-colors using hue which makes it easy to identify the normal tissue and the pathologically affected tissue, eliminating the influence of porphyrin even when the biological tissue section which includes porphyrin is observed.

Third Embodiment

Figure 17:
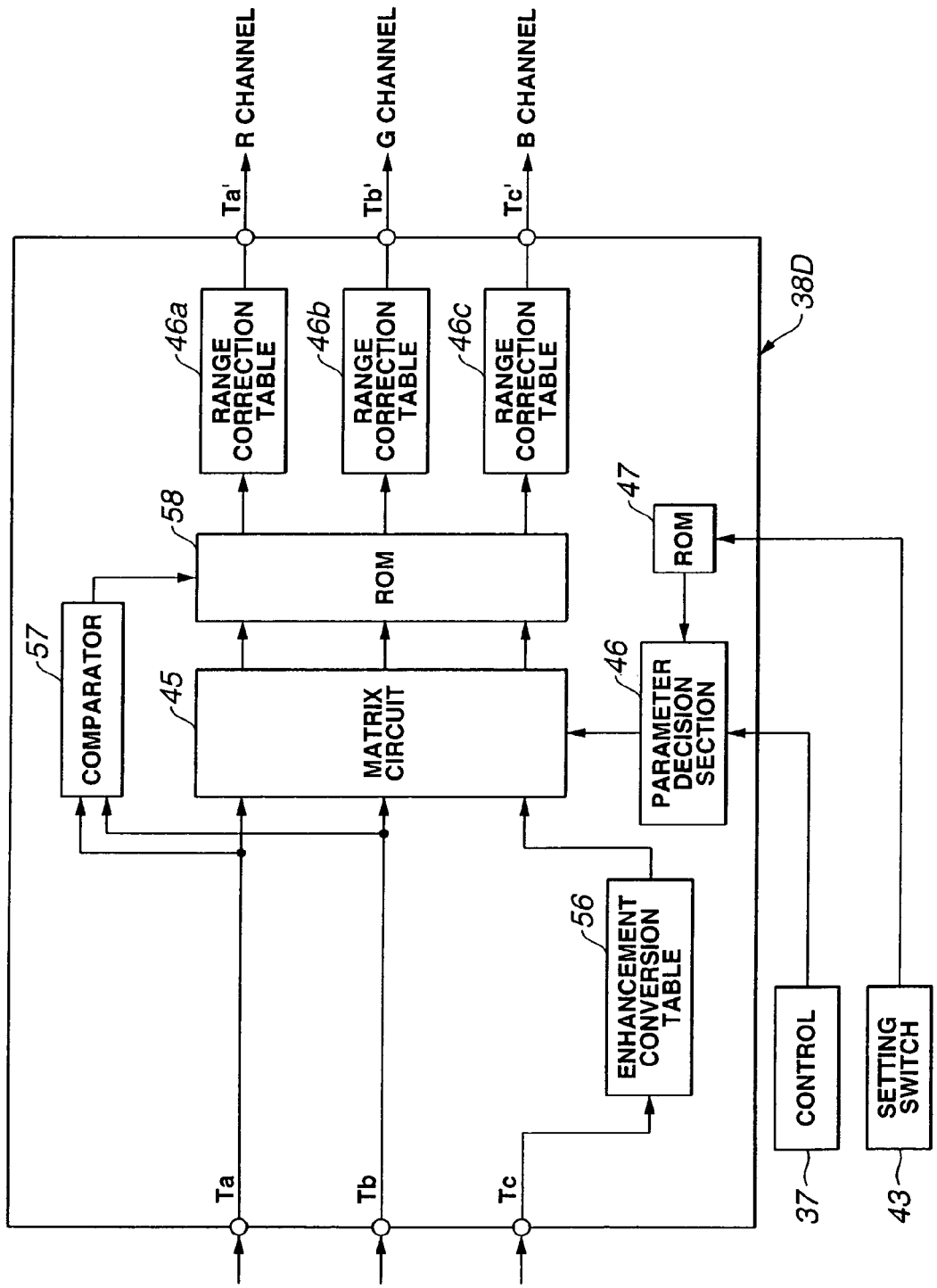

FIG. 17 shows the image processing circuit 38D of the third embodiment.

In this image processing circuit 38D, an enhancement conversion table 56, comparator 57, and ROM 58 are additionally installed to the configuration in FIG. 4.

According to the present embodiment, the enhancement conversion table 56 is installed between the input end Tc and the matrix circuit 45 in FIG. 4, and the signal EX of the fluorescent image is enhancement-processed by this enhancement conversion table 56, and is input to the matrix circuit 45.

The input ends Ta and Tb are connected to the matrix circuit 45, and are connected to the comparator 57, and by this comparator 57, it is detected whether the signals R1 and G1, to be input from the input ends Ta and Tb, deviate from a predetermined range, and the detection signal is input to the ROM 58 installed between the matrix circuit 45 and the range correction tables 46a to 46c.

The ROM 58 compares the luminance level of signals to be input from the input ends Ta and Tb and the upper limit value, and if the luminance level exceeds the upper limit level, the ROM 58 sets all the luminance levels of the three signals after conversion processing by the matrix circuit 45 to the same upper limit value, for example (in this case the image is displayed in white).

Figure 18:
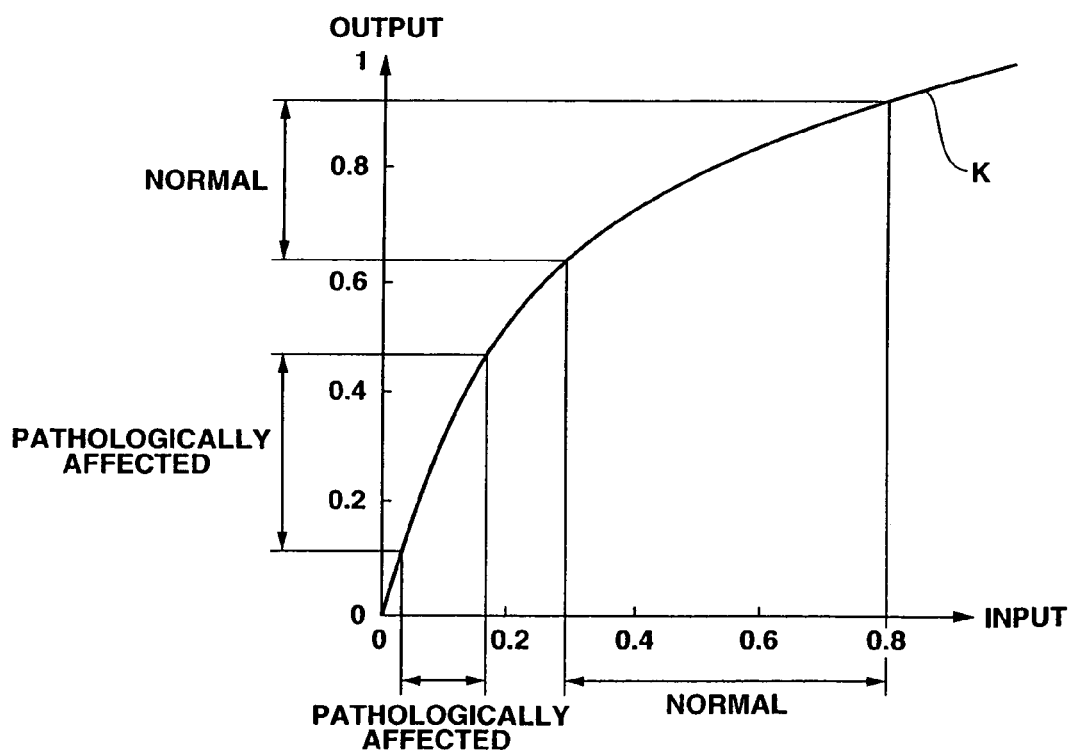
FIG. 17 and FIG. 18 are diagrams related to the third embodiment, where

The enhancement conversion table 56 is set to the input/output characteristic K, shown in FIG. 18, where the output level with respect to the signal at the pathologically affected tissue side at a low input level is expanded, and the range of the output level with respect to the signal at the normal tissue side at a wide input level is compressed to be small.

By this, the biased levels of the three signals to be input to the matrix circuit 45 are corrected and converted, so as to be input at a more desirable level.

In the normal-light mode, the enhancement conversion table 56 does not function, and input signals are output as is.

The other configuration is the same as the first embodiment.

According to the present embodiment, in addition to the same functions and effects of the first embodiment, the signal level of the fluorescent images is expanded, and the luminance level, when displaying in pseudo-colors, is increased, so that the hues and changes of tone can be identified more easily. (If the luminance level is low, identification of hue becomes difficult.)

Even when the level of input signal is low, the present embodiment allows a display with color tone at an appropriate level.

Fourth Embodiment

Figure 19:
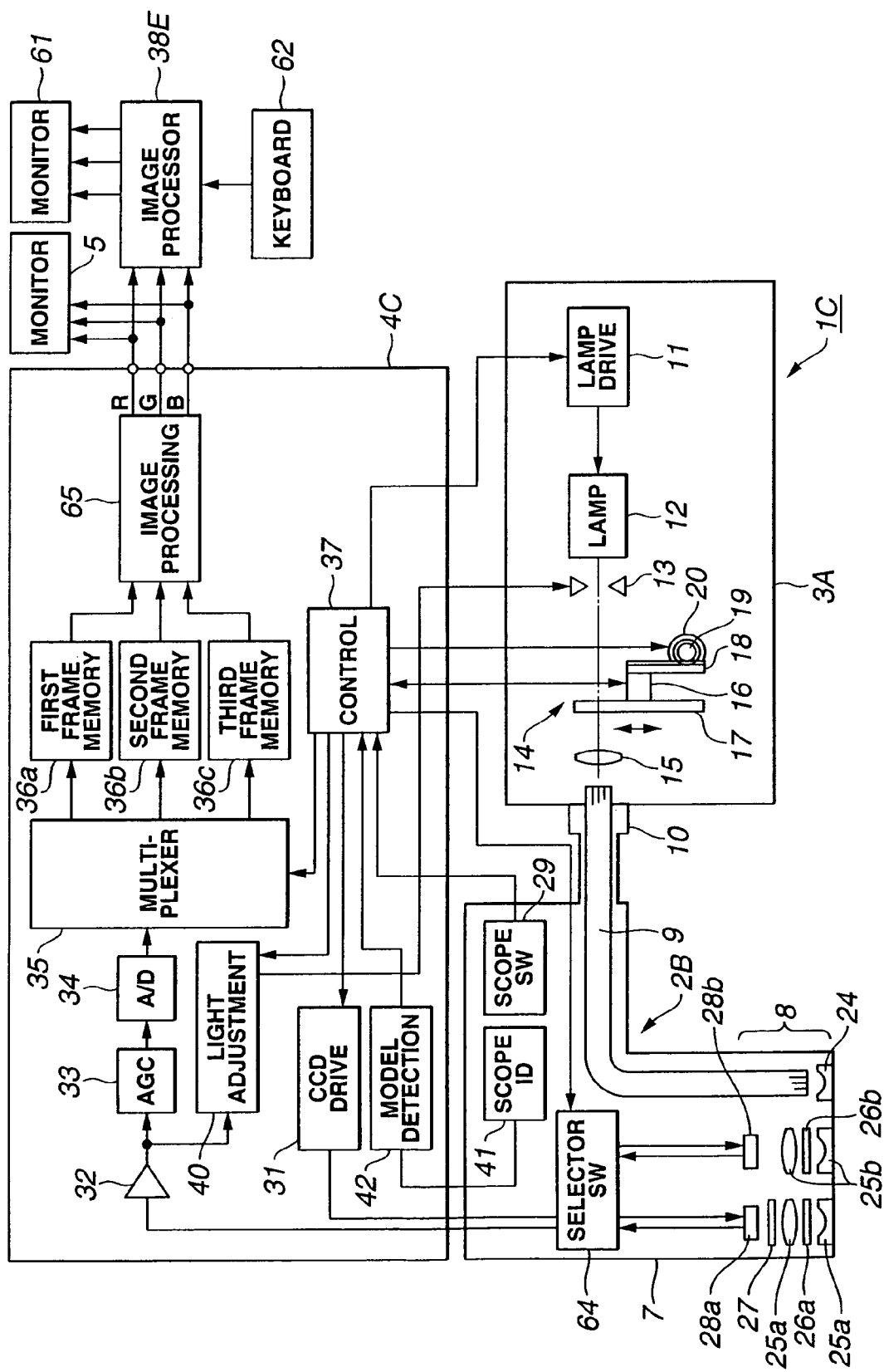
FIG. 19 to FIG. 25 are diagrams related to the fourth embodiment, where

Now the fourth embodiment of the present invention will be described with reference to FIG. 19 to FIG. 25. An endoscope system 1C, according to the fourth embodiment shown in FIG. 19, is comprised of an electronic endoscope (hereafter called "scope") 2B, a light source unit 3A for supplying illumination light, a processor 4C for executing signal processing, a monitor 5 for displaying images, an image processor 38E which is connected to the output end of the processor 4C, a monitor 61 which is connected to the output end of the image processor 38E, and a keyboard 62 which is connected to the image processor 38E.

In the endoscope system 1C, the scope 2B can be used. The scope 2B is a different model from the scope 2A in FIG. 1, housing two image pickup devices.

This scope 2B has a CCD for fluorescent observation (CCD for fluorescence) 28a, and a CCD for normal-light observation (CCD for normal-light use) 28b at the tip 8 of the insertion section 7.

On the observation window of the tip section 8, an image capturing section for fluorescent observation, which is comprised of an objective lens system 25a for forming an optical image, a first aperture 26a for spatially limiting the light quantity, an excitation light cut filter 27, and a CCD for fluorescent observation 28a as an image pickup device for capturing fluorescent images, and an image capturing section for normal-light observation, which is comprised of an objective lens system 25b for forming an optical image, a second aperture 26b, and a CCD for normal-light observation 28b as an image pickup device for capturing normal-light images, are installed. The fNo. of the first aperture 26a has a smaller value than the fNo. of the second aperture 26b. In other words, a large quantity of light enters the CCD for fluorescence 28a.

The two CCDs 28a and 28b are connected to the CCD drive circuit 31 and to the preamplifier 32 via a selector switch 64. Switching this selector switch 64 is controlled by the control circuit 37. In other words, when the fluorescent mode is selected by the scope switch 29, the CCD for fluorescence 28a is selected and used, and when the normal-light mode is selected, the CCD for normal-light use 28b is selected and used.

In the present embodiment as well, the scope 2B has a scope ID generation section 41 (for simplification, called "scope ID" in the drawings after FIG. 19), which generates unique identification information, including the type (model) thereof, so that a scope 2B, a different model, can be connected and used, and the model detection circuit 42 in the processor 4C detects the model using the scope ID.

The scope ID generation section 41 is comprised of a memory device, where information, including the model of the scope 2B, is written, however the scope ID generation section 41 is not limited to this, but can be comprised of a dip switch, which is further comprised of a plurality of switches, for example.

The model information detected by the model detection circuit 42 of the processor 4C is sent to the control circuit 37, and the control circuit 37 controls the light source unit 3C according to the detected model, so that a subject can be observed in the fluorescent mode or the normal-light mode which is suitable for the scope of that model.

The configuration of the light source unit 3A in the present embodiment is the same as the light source unit 3A in FIG. 1.

The excitation light cut filter 27 installed in front of the CCD 28a is set to have the transmission characteristic shown in FIG. 3C.

The processor 4C is the processor 4A in FIG. 1, wherein an image processing circuit 65 for processing image signal generation, such as gamma correction, is used instead of the image processing circuit 38. The signals to be output from the R, G and B channels of the image output ends of the processor 4C are output to the monitor 5, and are also output to the image processor 38E.

Figure 20:
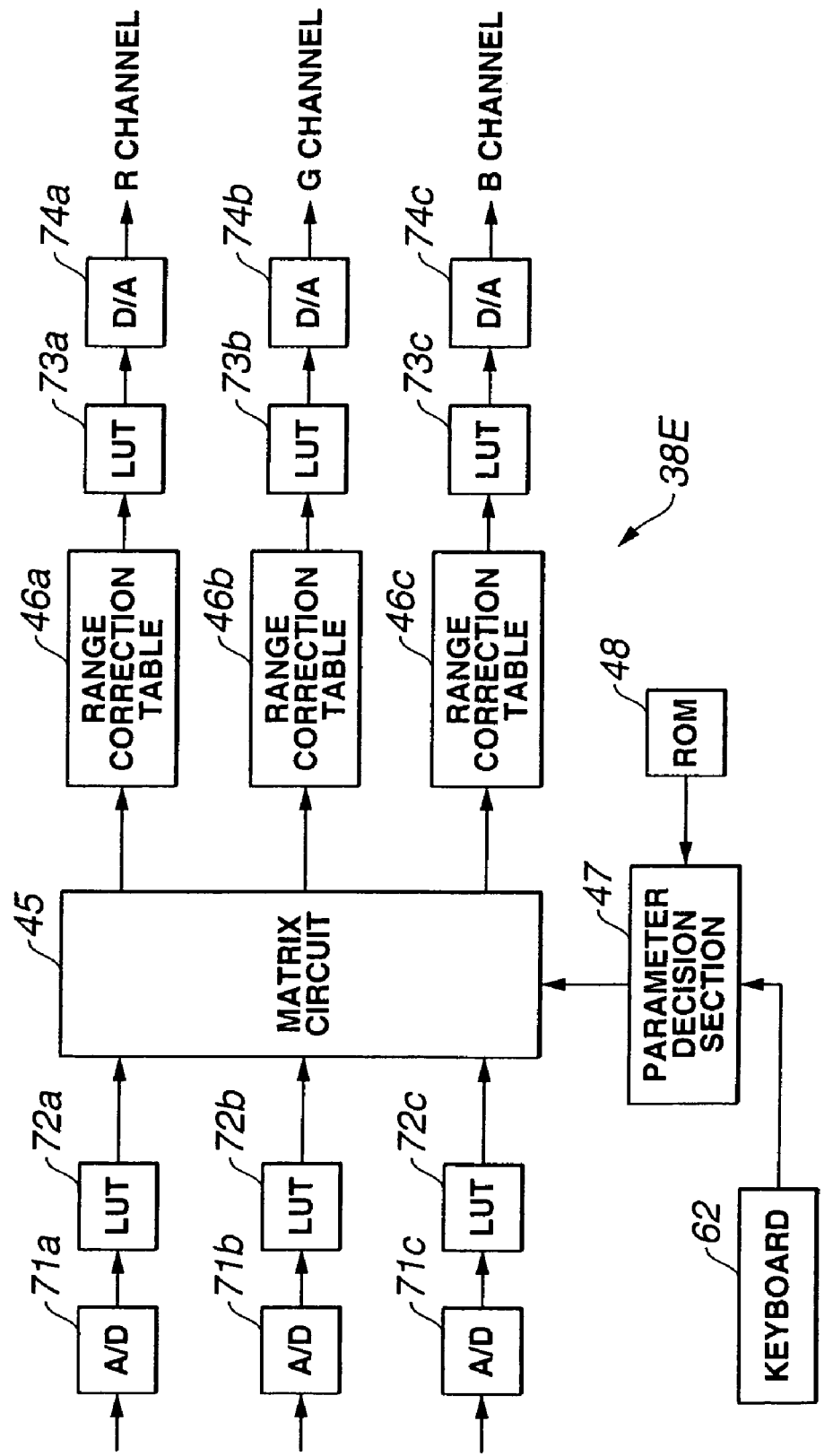

FIG. 20 shows the configuration of the image processor 38E.

This image processor 38E executes A/D conversion on analog signals to be output from the R, G and B channels of the processor 4C using the A/D conversion circuits 71a to 71c. The digital signals after A/D conversion are input to lookup tables 72a to 72c where inverse gamma correction is executed.

The signals after inverse gamma correction is executed are input to the matrix circuit 45, where the matrix conversion processing is executed just like the first embodiment, and range correction processing is executed for the output signals thereof by the range correction tables 46a to 46c.

The output signals of the range correction tables 46a to 46c are input to the lookup tables 72a to 72c, and after gamma correction is executed, the output signals are converted to analog signals by the D/A conversion circuits 74a to 74c, and are output to the monitor 61.

The parameter decision section 47 is connected to the matrix circuit 45, and the ROM 48 and the external keyboard 62 are connected to this parameter decision section 47.

Parameters to generate a plurality of sets of matrix elements are stored in the ROM 48, just like the first embodiment, and the matrix of the matrix circuit 45 is decided via the parameter decision section 47 by selection and control using the keyboard 62.

In the present embodiment, the processor 4C executes normal-light image processing, and the external image processor 38E executes the processing of images so that the normal tissue and the pathologically affected tissue can be easily identified in the fluorescent mode.

By using the scope 2B comprised of the CCD for fluorescent observation 28a and the CCD for normal-light observation 28b, images with better quality can be obtained in the respective modes compared with the case of a CCD sharing the respective functions.

The functions of the present embodiment will now be described.

When the scope 2B is connected to the processor 4B, the model detection circuit 42 detects the ID information from the scope ID circuit 41, and the control circuit 37 judges the model of the connected scope by the detection signal of the model detection circuit 42. And the control circuit 37 executes control operation according to the model which was judged.

When the normal-light mode is selected in the state where the scope 2B is connected, the control circuit 37 switches the selector switch 64 so as to select the CCD for normal-light observation 28*b*.

In the normal-light mode, the RGB filter 21 at the inner circle side of the switching filter section 14 is positioned on the optical path.

In the present embodiment, the excitation light cut filter 27 is not installed in the front of the CCD 28*b*, so the images of R, G and B are sequentially captured, just like the image capturing by a normal-light CCD.

Therefore in this mode, during the illumination period in B in the first embodiment, an increase in the lamp current is not required and images with good white balance can be captured and displayed.

When the fluorescent mode is selected, the control circuit 37 switches the selector switch 46 so as to select the CCD for fluorescent observation 28*a*.

The control circuit 37 controls the motor for moving 20 and moves the switching filter 17 so that the filter for fluorescent observation 51 is positioned on the illumination light path.

This case is the same state when the images are captured by the scope 2A in the first embodiment.

In the fluorescent mode, the amplification factor of the CCD 28*a* and the lamp current increase.

In this case, image signal generation processing is executed by the processor 4C, and image signals to be output from the R, G and B channels are input to the monitor 5, and are also input to the image processor 38E.

In this case, images are displayed on the monitor 5 in pseudo-colors without the matrix conversion processing in the first embodiment.

The image processor 38E executes processing similar to that executed by the image processing circuit 38 in the processor 4A in the first embodiment.

Since analog image signals, to be output to outside the processor 4C, are input to the image processor 38E, in the image processor 38E, the A/D conversion circuits 71*a* to 71*c* execute an A/D conversion, as shown in FIG. 20, and executes inverse gamma correction using the lookup tables 72*a* to 72*c*, so as to generate digital signals which are not gamma corrected.

The matrix circuit 45 executes matrix conversion processing, then executes range correction using the range correction tables 46*a* to 46*c*. Then gamma correction is executed using the lookup tables 72*a* to 72*c*, the signals are output from the R, G and B channels to the monitor 61 via the D/A conversion circuits 74*a* to 74*c*, and images similar to those described in the first embodiment are displayed on the display screen of the monitor 61.

According to the present embodiment, images can be captured without a part of the blue wavelength band being cut by the excitation light cut filter in the normal-light mode, and normal-light images with good S/N can be obtained.

In the fluorescent mode, images are displayed in pseudo-colors via the external image processor 38E in a state where the normal tissue and the pathologically affected tissue can be easily identified, just like those described in the first embodiment.

Figure 21:
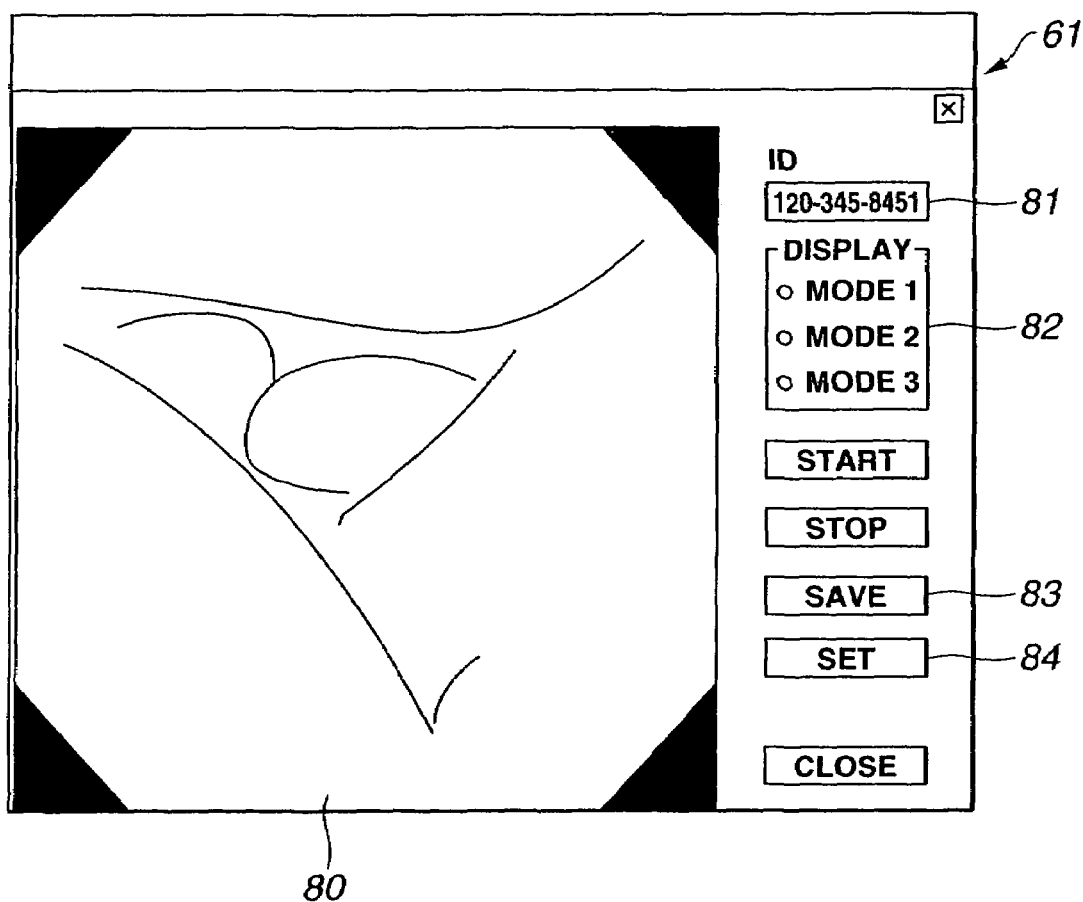

FIG. 21 shows an image example to be displayed on the monitor 61 connected to the image processor 38E. The image which is output by the image processor 38E is displayed in pseudo-colors on an image display section 80 on the display screen of the monitor 61.

In a box 81 next to the image display section 80, a directory for storing images is created for each patient ID to be input. Depending on the mode selected by a button 82, predetermined parameters of the matrix can be selected. Also an image display start button, stop button, save button 83, and a button 84 to call up the setting screen are disposed.

Figure 22:
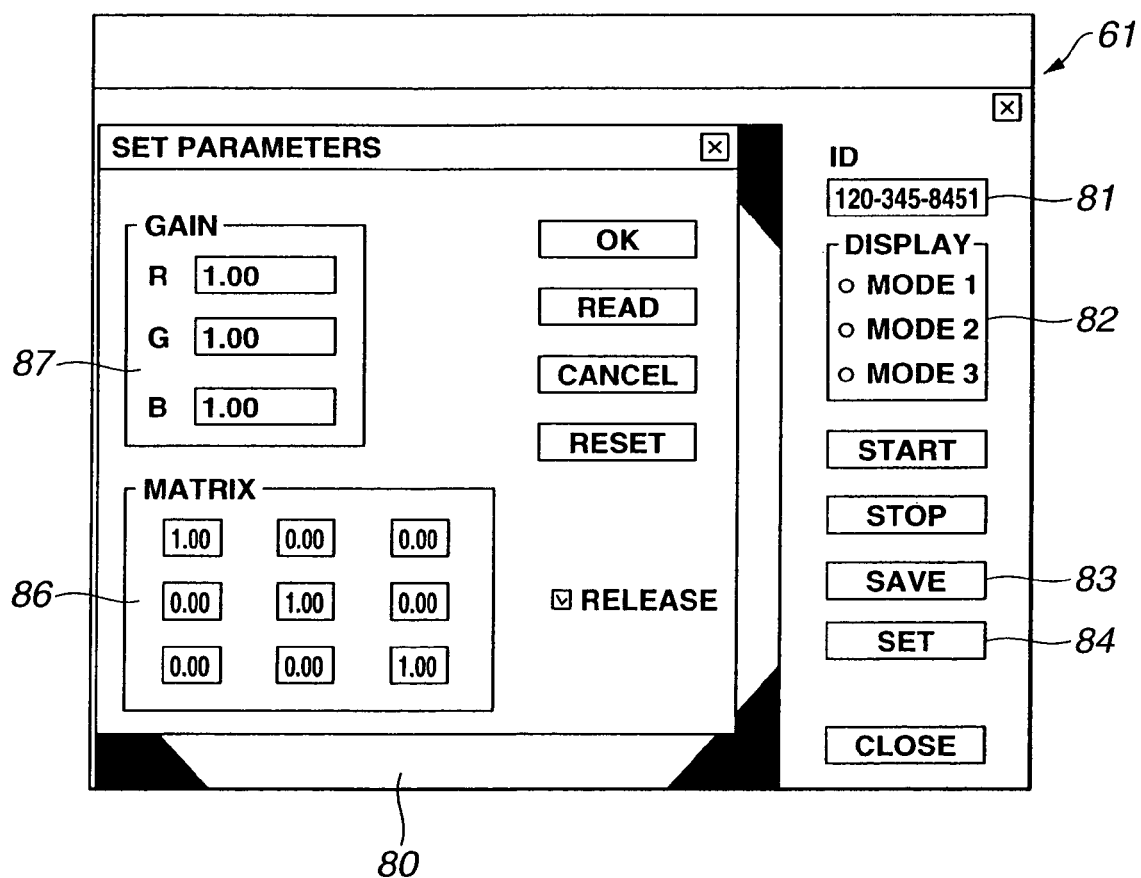

FIG. 22 shows a setting screen called up by operating the button 84. In this case, a box 86 for inputting the parameters of the matrix and a box 87 for setting the gain for the R, G and B channels are displayed on the image display section 80 in FIG. 21, so that the user can set the desired values.

Figure 23:
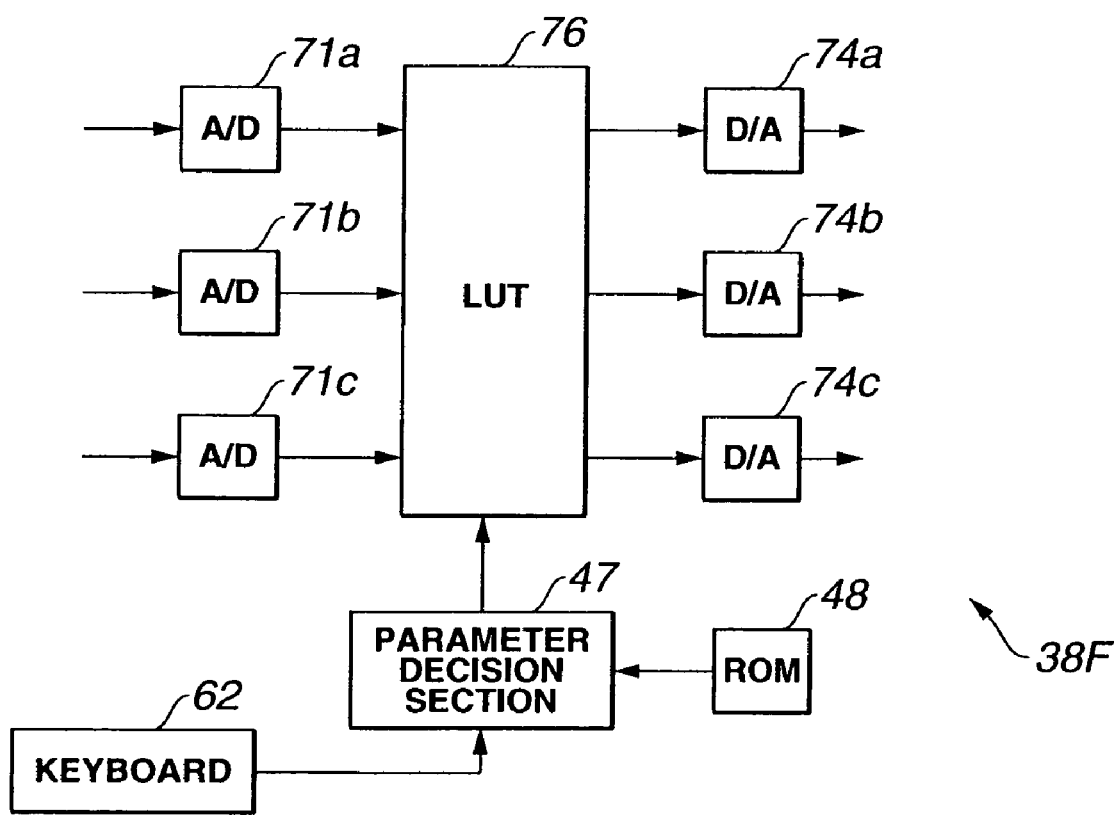

FIG. 23 shows an image processor 38F of the first variant form. In this image processor 38F, the functions of the lookup tables 72*a* to 72*c*, the matrix circuit 45, the range correction tables 46*a* to 46*c*, and the lookup tables 73*a* to 73*c* in FIG. 20 are all integrated into the lookup table 76.

According to the present variant form, cost can be decreased.

Figure 24:
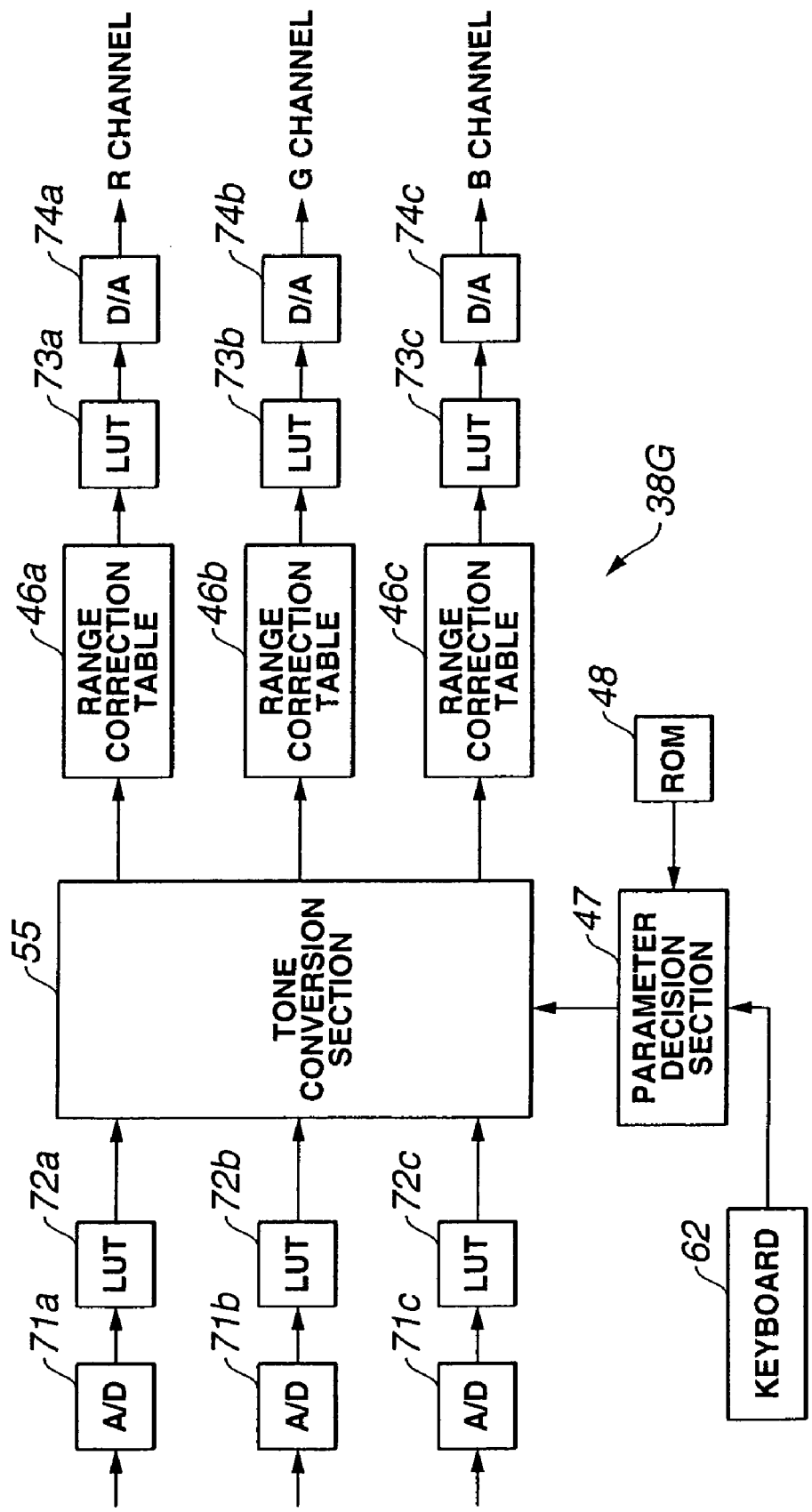

FIG. 24 shows an image processor 38G of the second variant form. In this image processor 38G, the matrix circuit 45 in FIG. 20 has been changed to the color tone conversion section 55. This variant form has functions and effects similar to the third embodiment.

Figure 25:
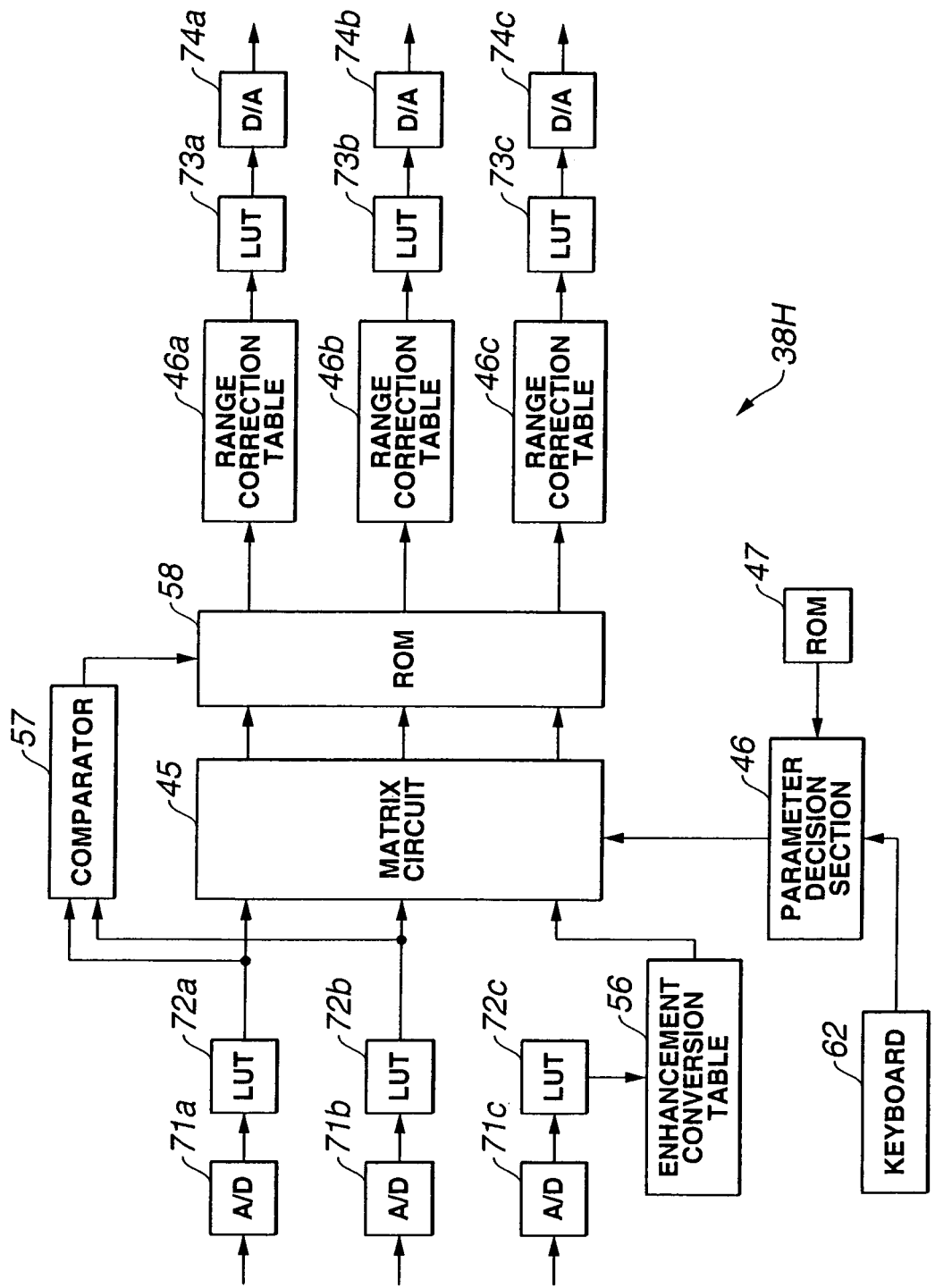

FIG. 25 shows an image processor 38H of the third variant form. This image processor 38H corresponds to FIG. 17.

In other words, in the image processing circuit 38D in FIG. 17, the A/D conversion circuits 71*a* to 71*c* and the lookup tables 72*a* to 72*c* are installed at the input side, just like FIG. 20, and the lookup tables 73*a* to 73*c* and the D/A conversion circuits 74*a* to 74*c* are installed at the output side, and the keyboard 62 is connected to the parameter decision section 46.

This variant form has functions and effects similar to the third embodiment.

Fifth Embodiment

Now the fifth embodiment of the present invention will be described with reference to FIG. 26 to FIG. 34. The object of the present embodiment is to provide an endoscope system which can obtain both fluorescent images and normal-light images with good image quality, even if a different endoscope (scope) is used.

Figure 26:
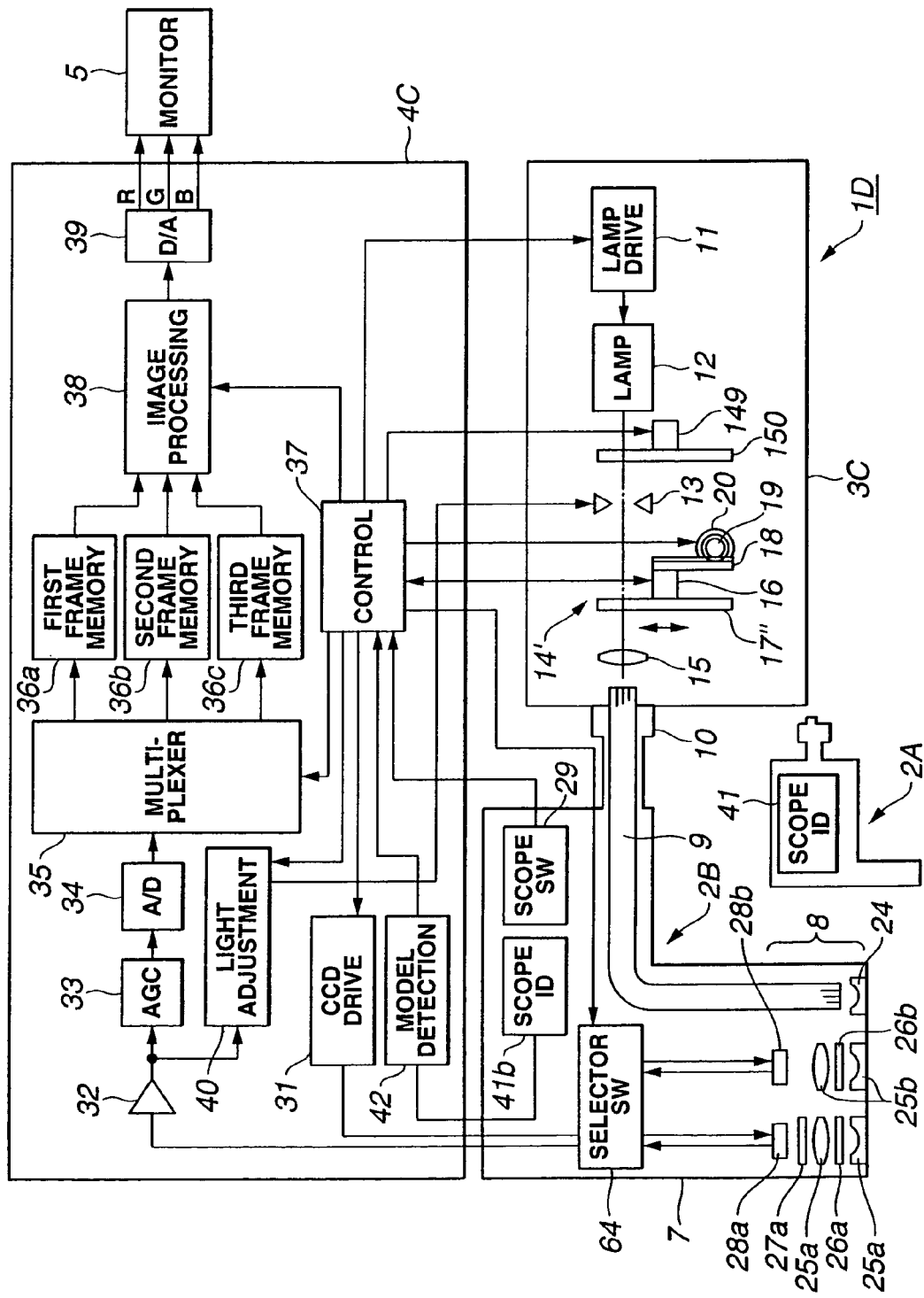

An endoscope system 1D of the fifth embodiment shown in FIG. 26 is comprised of a first and second electronic endoscopes (hereafter "scopes") 2A and 2B, a light source unit 3C for supplying illumination light, a processor 4C for executing signal processing, and a monitor 5 for displaying images.

In this embodiment as well, each scope 2A and 2B has scope ID generation section (simply called "scope ID" in FIG. 26, as mentioned above) 41 and 41*b* for generating unique identification information, including the type (model) of the scopes 2A and 2B respectively, so that the first and second scopes 2A and 2B, which are different types, can be connected. The scope ID circuits 41 and 41*b* are comprised of a memory device, where information, including the model of the scopes 2A and 2B, is written respectively, but the scope ID circuit is not limited to this, but may be comprised of a dip switch, which is further comprised of a plurality of switches, for example.

At the processor 4C side, the model detection circuit 42 for identifying identification information of the connected scopes 2A and 2B is installed, where the model information detected by the model detection circuit 42 is sent to the control circuit 37, and the control circuit 37 controls the light source unit 3C so that the subject can be observed in the fluorescent mode or the normal-light mode suitable for the scope of the detected model.

The light source unit 3C of the present embodiment is the light source unit 3A in FIG. 1, wherein a switching filter 150, where the rotation position is switched by a motor 149, is installed between the light source aperture 13 and the lamp 12.

As described later, this switching filter 150 has at least one filter for limiting the wavelength of the excitation light to be irradiated onto the subject side according to the scope 2A or 2B to be connected and used in the fluorescent mode, in addition to the filter for transmitting the wavelength band of the visible light without limitation. And according to the scope ID circuit 41 or 41b, or according to the observation conditions, a plurality of filters (filter for not limiting the band and at least one (two in this embodiment) filter for limiting the band) installed at the switching filter 150 can be switched and used.

For a switching filter section 14' in the present embodiment, a switching filter 17", which is somewhat different from the switching filter 17 in the switching filter section 14 in FIG. 1, is used.

Figure 27A:
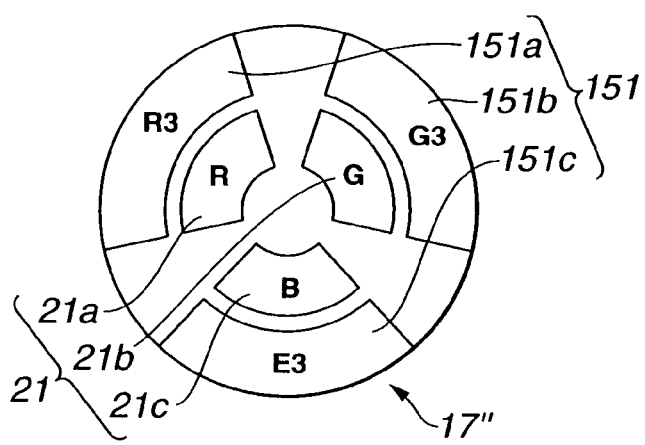
FIG. 27A and FIG. 27B are diagrams depicting a configuration of the two switching filters installed on the light source unit.

As FIG. 27A shows, in this switching filter 17", the RGB filter 21 for normal-light observation is installed at the inner circle side, and the filter for fluorescent observation 151 is installed at the outer circle side.

In this switching filter 17", the RGB filter 21 for normal observation is disposed concentrically at the inner circle side, and a filter 151 for fluorescent observation, which is comprised of the R3, G3 and E3 filters 151a, 151b and 151c, is disposed concentrically at the outer circle side. And according to the switching of the normal-light mode and the fluorescent mode, the RGB filter 21 at the inner circle side or the filter 151 for fluorescent observation at the outer circle side is selected.

Figure 28A:
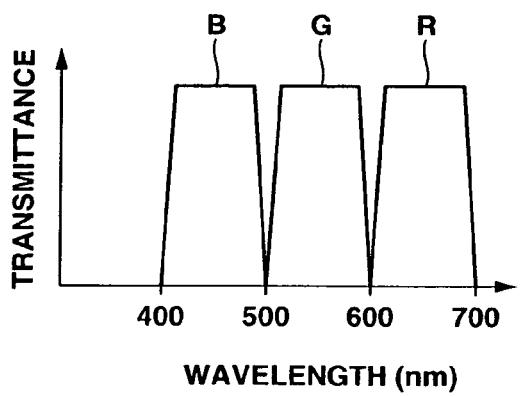
FIG. 28A to FIG. 28D are diagrams depicting the transmission characteristic with respect to the wavelength of the RGB filter and the filters for fluorescent observation.

The RGB filter 21 for normal-light observation at the inner circle side, shown in FIG. 28A, has the same transmission characteristic as in FIG. 3A. In other words, it is set such that the R filter 21a transmits light of a wavelength band ranged from 600 to 700 nm, the G filter 21b transmits from 500 to 600 nm, and the B filter 21c transmits from 400 to 500 nm respectively.

Figure 28B:
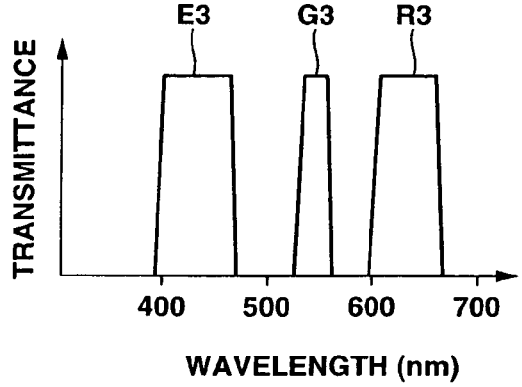

The filter 51 for fluorescent observation disposed at the outer circle side is comprised of the R3, G3 and E3 filters 151a, 151b and 151c, and the transmission characteristic thereof is set to have the characteristic shown in FIG. 28B. In other words, it is set such that the R3 filter 151a transmits 600 to 660 nm, the G3 filter 151b transmits 540 to 560 nm, and the E3 filter 151c transmits 400 to 470 nm wavelength bands respectively.

Figure 27B:
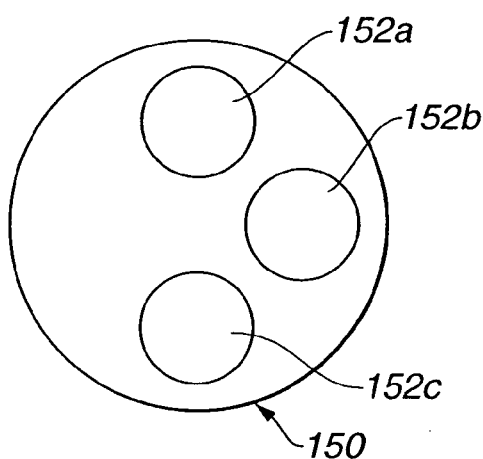

FIG. 27B is a diagram depicting the arrangement of the switching filter 150, where three filters, 152a, 152b and 152c, are arranged in a circumferential direction. According to the switching of the normal-light observation or the fluorescent observation mode, the model, the scope or the mode according to the conditions of fluorescent observation (user selection) (e.g. mode to view information on a deeper area, mode assigning priority to brightness), the rotation position of the switching filter 150 is controlled, and one of the first filter 152a, second filter 152b and third filter 152c is set on the optical path.

Figure 28C:
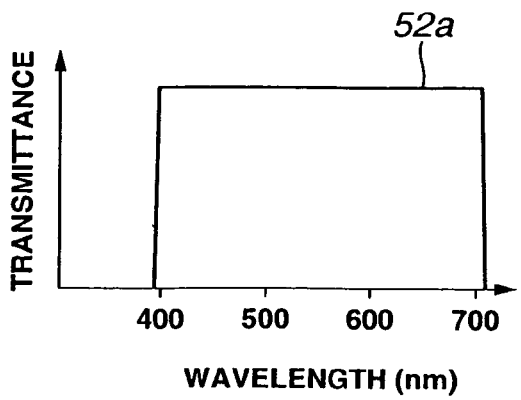

The first filter 152a transmits light in the entire wavelength band of visible light, from blue to red, as shown in FIG. 28C. In the normal-light mode, the control circuit 37 controls the motor 49, so that the first filter 152a is positioned on the optical path.

Figure 28D:
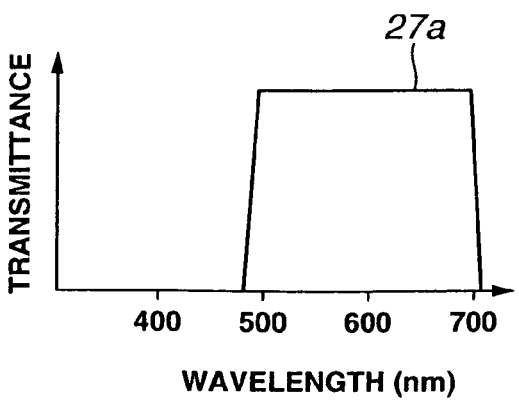

An excitation light cut filter 27a, installed in front of the CCD 28a, is set to have the transmission characteristic shown in FIG. 28D. Concretely, this excitation light cut filter 27a transmits light in the 490 to 700 nm wavelength band, that is, visible light, excluding a part of the blue band at the shorter wavelength side.

Figure 29A:
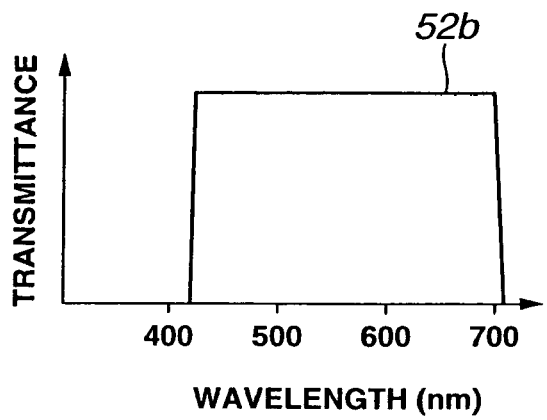
FIG. 29A and FIG. 29B are diagrams depicting the transmission characteristic with respect to the wavelength of the second and third filters.
Figure 29B:
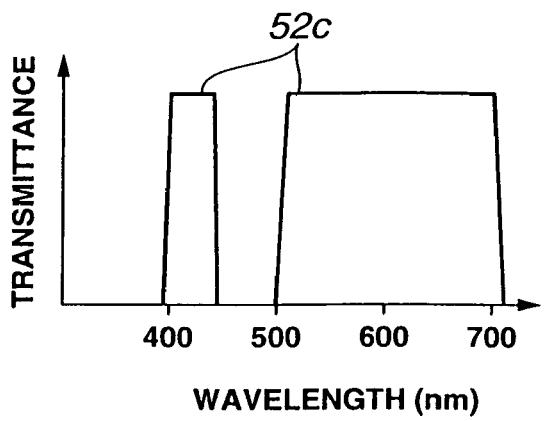

The second filter 152b and the third filter 152c, shown in FIG. 27B, are set to have the transmission characteristic shown in FIG. 29A and FIG. 29B respectively. The second filter 152b transmits light in the 430 to 700 nm wavelength band. The third filter 152c transmits a part of blue in 400 to 440 nm and green and red light in the 500 nm or higher wavelength band.

The second scope 2B is connected to this second filter 152b, and when the fluorescent mode is selected, the user can select one of the two filters, the second filter 152b or the first filter 152a, according to the observation conditions.

The first scope 2A, which is shown in detail in FIG. 1, is connected to the third filter 152c, and can be used when the fluorescent mode is selected. The other configuration is the same as the first embodiment.

The functions of the present embodiment will now be described.

When the first scope 2A or 2B is connected to the processor 4B, the model detection circuit 42 detects the ID information from the scope ID circuit 41 or 41b, and the control circuit 37 judges the model of the connected scope by the detection signal of the model detection circuit 42. And the control circuit 37 executes control operation according to the model which was judged.

When the normal-light mode is selected in the state where the second scope 2B is connected, for example, the control circuit 37 switches the selector switch 64 so as to select the CCD for normal-light observation 28b.

Figure 30A:
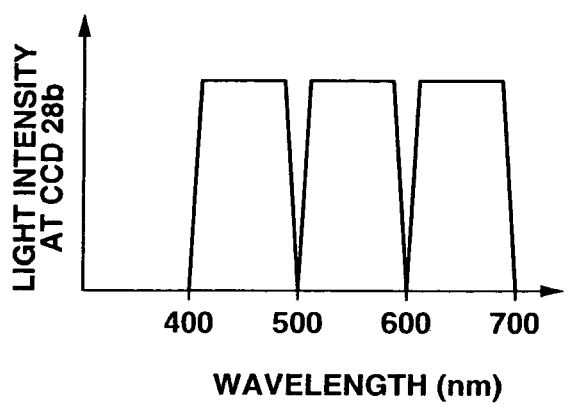
FIG. 30A and FIG. 30B are diagrams depicting the light intensity characteristic of light to be received by the respective CCD when a white subject is observed in normal-light observation mode, and when skin is observed in fluorescent observation mode.

In the normal-light mode, the RGB filter 21 at the inner circle side of the switching filter section 14' is positioned on the optical path, or the first filter 152a of the switching filter 150 is positioned on the optical path. FIG. 30A shows the light intensity received by the CCD 28b when a white subject is observed in this state.

In FIG. 3C, a part of the blue wavelength band is cut by the excitation light cut filter 27, but in the present embodiment, the excitation light cut filter is not installed in front of the CCD 28b, and R, G and B images are sequentially captured just like image capturing by a normal-light CCD. Therefore in this mode, during the illumination period in B in the first embodiment, an increase in the lamp current is not required and images with good white balance can be captured and displayed.

When the fluorescent mode is selected, the control circuit 37 switches the selector switch 64 so as to select the CCD for fluorescent observation 28a.

The control circuit 37 controls the motor for moving 20, and moves the switching filter 17" so that the filter for fluorescent observation 151 is positioned on the illumination light path. In the switching filter 150, the first filter 152a remains on the illumination light path.

Figure 30B:
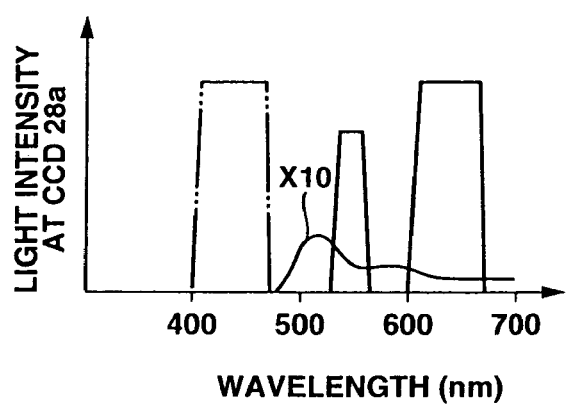

In this case, the excitation light, with a relatively wide band indicated by E3 in FIG. 28B, is irradiated as an excitation light transmitted through the first filter 152a and through the E3 filter 151c for fluorescent observation, and this excitation light is almost completely shielded by the excitation light cut filter 27a installed in front of the CCD 28a (indicated by the two-dotted chain line in FIG. 30B). In the present embodiment, the wavelength band of the excitation light is increased so that the irradiation energy thereof is increased, and the light intensity of fluorescence to be generated is increased.

With illumination by R3 and G3, the reflected lights thereof are received by the CCD 28a without being shielded by the excitation light cut filter 27a. In the fluorescent mode, the amplification factor of the CCD 28a and the lamp current increase.

Therefore, in the case of the scope 2B, which has the CCD for fluorescent observation 28a, and the CCD for normal-light observation 28b, images with good quality can be obtained in the respective modes compared with the case of a CCD 28 and scope 2B sharing the respective functions.

In the normal-light mode, for example, images can be captured without a part of the blue wavelength band being shielded by the excitation light cut filter 27, and normal-light images with a good S/N can be obtained. In the fluorescent mode as well, the wavelength band of the excitation light can be widened, so an excitation light with a higher energy intensity can be irradiated, and a fluorescent image with a good S/N can be obtained by increasing the intensity of fluorescence to be generated by the excitation light.

Also according to the present embodiment, the second filter 152b can be selected to obtain information on a deeper area in the fluorescent mode. This selection can be executed by the scope switch 29, for example.

If this selection is made, the control circuit 37 rotates a motor 149 for 90° so that the second filter 152b, instead of the first filter 152a, is positioned on the optical path.

This second filter 152b has the characteristic to cut the shorter wavelength side of blue, as shown in FIG. 29A, compared with the transmission characteristic of the first filter 152a (shown in FIG. 28C).

Figure 31:
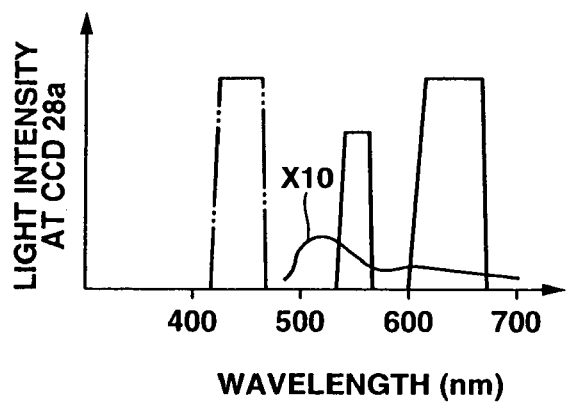

Therefore FIG. 31 shows the case when skin is observed in the fluorescent mode of this selection. In this case, most of the excitation light reaches the deep area of the tissue, so the influence of self-fluorescence by porphyrin can be decreased by increasing the intensity of the fluorescence from the deep area side, eliminating the excitation light around 400 nm, which is the excitation wavelength of porphyrin.

Instead of the excitation light cut filter 27a with the characteristic shown in FIG. 28D, an excitation light cut filter 27a' with the characteristic shown in FIG. 32A may be used. This excitation light cut filter 27a' is set so as to transmit 490 to 620 nm. (Therefore, red light at a 620 nm or 630 nm or more wavelength is not transmitted.) In this way, the excitation light cut filter 27a' is set such that the fluorescent band of porphyrin, that is, a part of red, is shielded.

FIG. 32B shows a case when skin is observed using the excitation light cut filter 27a'. In this case, the component of self-fluorescence by porphyrin can be decreased even more.

In the present embodiment, the scope 2A described for the first embodiment can be connected and used.

When this scope 2A is used, the motor for moving 20 is driven by the control of the control circuit 37 in the normal-light mode, and the RGB filter 21 at the inner circle side is positioned on the optical path in the switching filter section 14'.

In the switching filter 150, the first filter 152a is positioned on the illumination light path. And RGB is irradiated from the tip of the scope 2A. In this case, the excitation light cut filter 27 is in front of the CCD 28 of the scope 2A, so a part of the wavelength of the B light is shielded, and the reflected lights of the B light, the R light and the G light, which are limited to 460 nm to 500 nm, are captured by the CCD 28.

Therefore, when an image of a white subject is captured in this case, the light intensity to be received by the CCD 28 is as shown in FIG. 33A.

In this case, the control circuit 37 activates the electronic shutter functions when B light is illuminated, as described for the first embodiment.

When the fluorescent mode is selected, the switching filter 17" is moved by the motor for moving 20, and the filter for fluorescent observation 151 is positioned on the optical path. The third filter 152c is positioned on the optical path in the switching filter 150.

FIG. 33B shows the characteristic of the light intensity received by the CCD 28 when the skin is observed in this fluorescent mode. The excitation light at 400 to 440 nm from E3, G3 and R3, are irradiated from the tip of the scope 2A. Since the excitation cut filter 27 is in front of the CCD 28, the excitation light at 400 to 440 nm is completely shielded, and fluorescence excited by the excitation light at 400 to 440 nm and the reflected light of the R light and G light are captured by the CCD 28.

FIG. 34A shows a display example of images on the monitor 5.

In the patient information display area 5b at the left side of the endoscope image display area 5a of the monitor 5 as shown in FIG. 34A, for example, the ID, name and other information of a patient are displayed, and below this patient information display area 5b, the mode display area 5c for displaying the observation mode (simply called "mode" in FIG. 34A) is provided.

In the mode display area 5c, the normal-light mode (white light mode) or the fluorescent mode is displayed as shown in detail in FIG. 34B, and in the fluorescent mode, brightness priority mode and depth information priority mode are displayed. The model of the connected scope may also be displayed.

The present embodiment having such a configuration and functions has the following effects.

The present embodiment can be used with the scope 2A described in the first embodiment, and also with the scope 2B, which houses an image pickup device for normal-light observation and an image pickup device for fluorescent observation respectively.

When the scope 2A described in the first embodiment is connected, the following effect is exhibited.

In the case of the electronic endoscope 2A, both a normal-light image and a fluorescent image can be displayed by installing one image pickup device at the tip 8 of the insertion section 7.

Therefore, compared with the case of housing a plurality of image pickup devices, the diameter of the insertion section of the electronic endoscope 2A can be decreased, the application range where the endoscope can be inserted and used can be increased, and the pain caused to a patient at insertion can be decreased. And an operator can insert the endoscope into a body cavity easily. Also cost can be decreased since only one image pickup device is used.

Since blue in the wavelength band (region) of visible light is used for the excitation light, a halogen lamp or a Xenon lamp, which can be used for normal-light illumination (white illumination), can be used for the lamp 12 of the light source unit 3A. Also compared with the case when ultraviolet is used for the excitation light, transmission loss due to the light guide fiber 9 can be decreased, and a component for normal-light information can be used, which are merits.

Also when the excitation light is irradiated onto a human body, the excitation light can be irradiated only on the surface of the body if ultra-violet is used, but in the case of blue light, the excitation light can be irradiated onto tissue at a deeper area.

When the scope 2B, where two image pickup devices for normal-light observation and fluorescent observation are housed, is connected, a normal-light image and a fluorescent image with better S/N can be obtained.

In FIG. 26, the scopes 2A and 2B have the scope ID circuits 41a and 41b for generating a unique ID (identification information), including the model thereof respectively. The model information may be simply input to the processor 4C.

Also in FIG. 26, the case of two types of scopes 2A and 2B was described for simplification, but the present embodiment can also be applied to the case when the scope ID circuit 41 is not installed in one scope, scope 2A for example. In other words, in this case, the scope ID is not generated when the scope 2A is connected to the processor 4C, so the control circuit 37 judges that the model of the scope 2A is connected by the output of the model detection circuit 42, and executes control operation accordingly.

Figure 35:
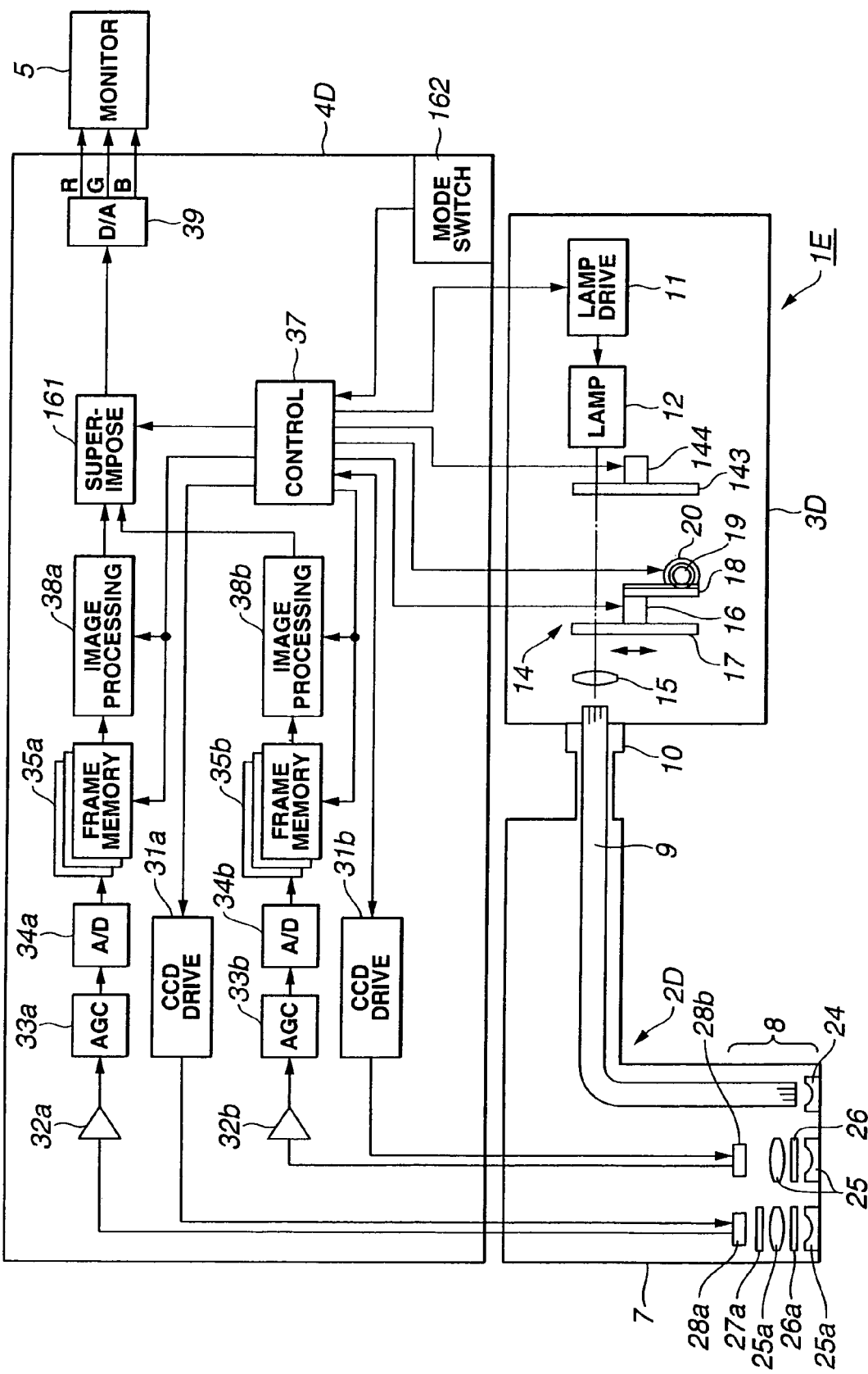

FIG. 35 shows the configuration of the endoscope system 1E according to the first variant form of FIG. 26. The endoscope system 1E is comprised of the scope 2D, light source unit 3D, processor 4D, and monitor 5.

The scope 2D is the scope 2B in FIG. 26, wherein the scope switch 29, the scope ID circuit 41b and the selector switch 64 do not exist. In other words, this scope houses the CCD for fluorescent observation CCD 28a and the CCD for normal-light observation 28b.

The light source unit 3D is the light source unit 3A in FIG. 1, wherein the light source aperture 13 does not exist, and a switching filter 143 is installed at the position of the light source aperture 13.

The rotation position of the switching filter 143 is controlled by a motor 144, and the rotary filter 17, which is rotated by the motor for rotation 16, is installed in front of the switching filter 143.

Figure 36A:
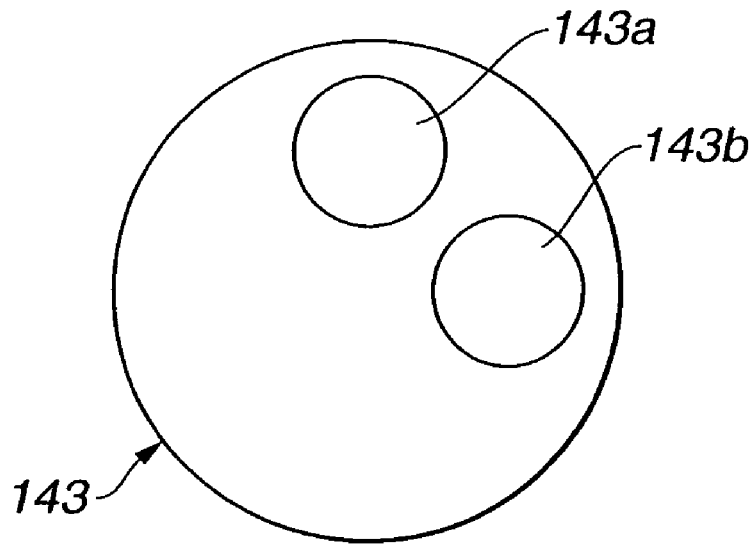
FIG. 36A and FIG. 36B are diagrams depicting respectively a configuration of the switching filter and the transmission characteristic thereof.

In the switching filter 143, a first filter 143a and a second filter 143b are installed at two locations in the circumferential direction, as shown in FIG. 36A. The first filter 143a is made of glass, for example, and transmits all the visible light from the blue band to the red band, as shown by the broken line in FIG. 36B.

Figure 36B:
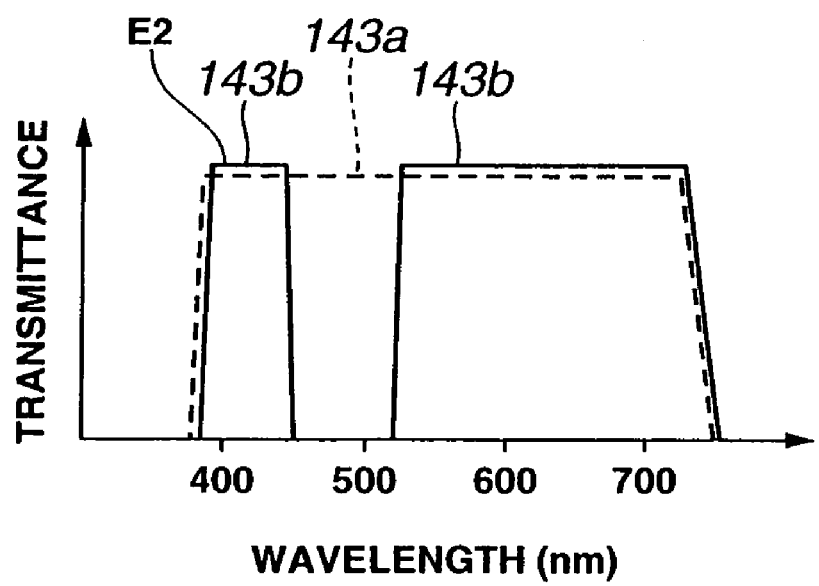

The second filter 143b is a band limiting filter where an interference film is deposited on such a substrate as BK7 and quartz, for example, and as shown by the solid line in FIG. 36B, the second filter 143b has a transmission characteristic to shield 450 nm to 510 nm of light. In other words, the second filter 143b is comprised of the filter characteristic part which transmits the shorter wavelength side of blue, which is used as the excitation light (the excitation light transmitted through this filter part is denoted as E2), and a part which transmits green and red.

The processor 4D essentially drives the two CCDs 28a and 28b respectively, and processes signals using respective dedicated processing circuits for each output signal to create the fluorescent images and the normal-light images.

Concretely, the CCD 28a is driven by the CCD drive circuit 31a, and the output signal of the CCD 28a is processed by the processing circuit for fluorescent images.

In other words, the output signal of the CCD 28a is amplified by the preamplifier 32a, and is further amplified up to a predetermined level by an AGC circuit 33a.

The output signal is converted into a digital signal by an A/D conversion circuit 34a, and is temporarily stored in a frame memory 35a, which is controlled by the timing control circuit 37.

The image data stored in this frame memory 35a is read under the control of the control circuit 37, and is input to an image processing circuit 38a.

The CCD 28b is driven by the CCD drive circuit 31b, and the output signal of the CCD 28b is processed by the processing circuit for normal-light images.

In other words, the output signal of the CCD 28b is amplified by the preamplifier 32b, and is further amplified to a predetermined level by the AGC circuit 33b.

The output signal is converted into a digital signal by the A/D conversion circuit 34b, and is temporarily stored in the frame memory 35b, which is controlled by the timing control circuit 37.

The image data stored in this frame memory 35b is read under the control of the timing control circuit 37, and is input to the image processing circuit 38b.

The image data for which such processing as contour highlighting is executed by the image processing circuits 38a and 38b is input to a superimpose circuit 161, and if necessary, both signals can be superimposed. The output signal of the superimpose circuit 161 is converted into an analog RGB signal by the D/A conversion circuit 39, and is output to the monitor 5.

The processor 4D has a mode switch 162, so that images in fluorescent mode and in normal-light mode can be obtained by operating this mode switch 162.

A mode to observe a subject by sequentially switching the fluorescent mode and the normal-light mode is also available, and in this case, both signals can be superimposed by the superimpose circuit 161 so that a fluorescent image and a normal-light image can be simultaneously displayed next to each other on the monitor 5.

In this first variant form, if this endoscope system is used in normal-light mode, for example, the RGB filter 21 of the rotary filter (switching filter) 17 is positioned on the illumination light path, and in the switching filter 143, the first filter 143a is positioned on the illumination light path, and is used.

In the fluorescent mode, the filter for fluorescent observation 22 of the switching filter 17 is positioned on the illumination light path, and in the switching filter 143, the second filter 143b is positioned on the illumination light path, and is used.

In FIG. 35, the D/A conversion circuit 39 is shared by the fluorescent image processing circuit and by the normal-light image processing circuit, but the dedicated D/A conversion circuit 39 may be used respectively.

As described in the fifth embodiment, this first variant form allows obtaining fluorescent images and normal-light images with good S/N when the scope 2D, where the CCD for fluorescent observation 28a and the CCD for normal-light observation 28b are housed and used.

Figure 37:
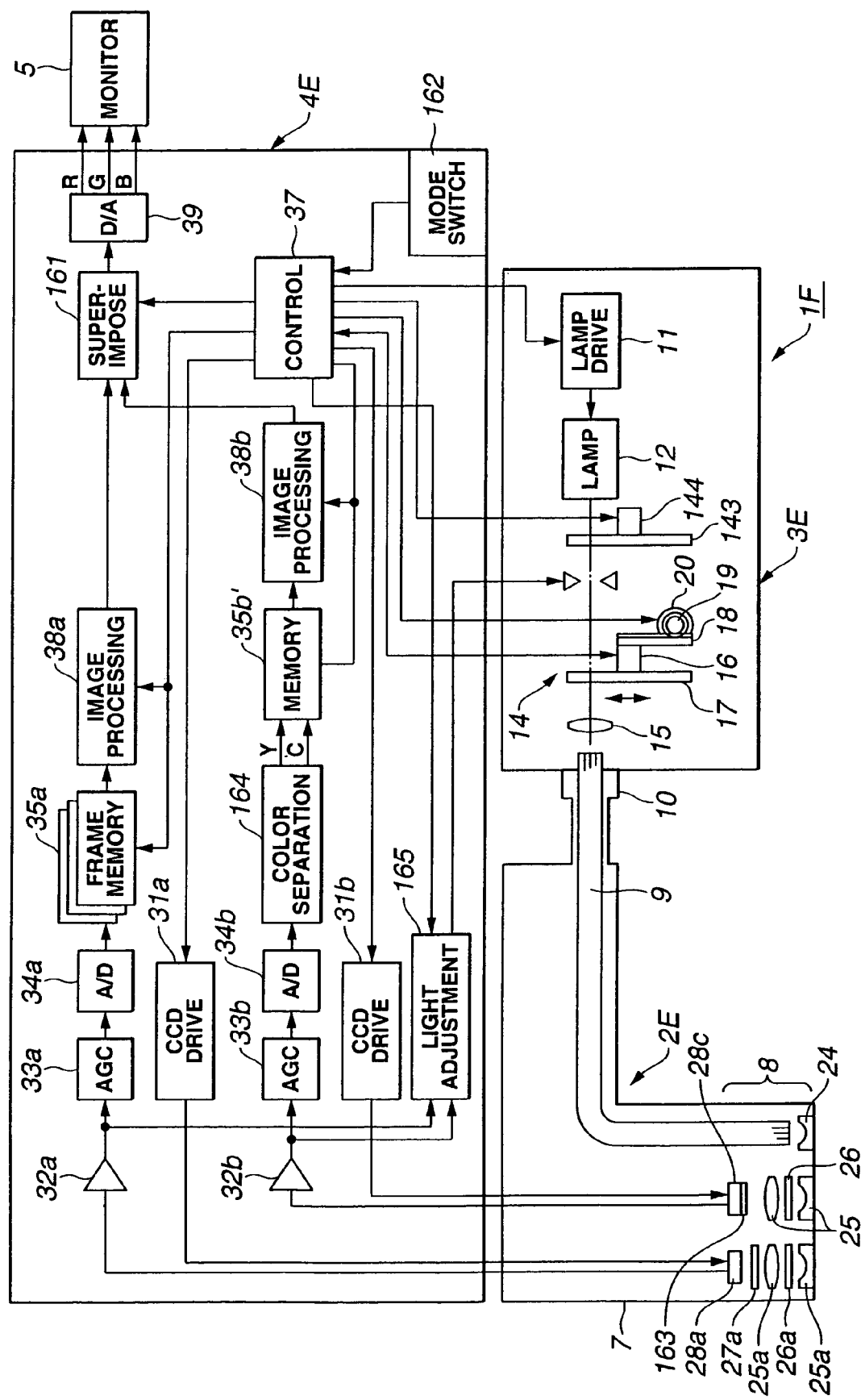

FIG. 37 shows a configuration of the endoscope system 1F according to the second variant form of FIG. 26. This endoscope system 1F is comprised of the scope 2E, light source unit 3E, processor 4E, and monitor 5.

The scope 2E is the scope 2D in FIG. 35, wherein the color CCD 28c, which has a color filter for optically separating colors, such as a mosaic filter 163, is used instead of the CCD 28b.

The light source unit 3E is the light source unit 3D in FIG. 35, wherein the switching filter 17" in FIG. 26 is used instead of the switching filter 17, and the light source aperture 13 is also installed.

The processor 4E is the processor 4D in FIG. 35, wherein a color separation circuit 164 for executing color separation on the output signals of the AGC circuit 33b is installed, and the Y/C component signal of the luminance signal Y and the color signal C, separated by the color separation circuit 164, is converted into a digital signal by the A/D conversion circuit 34b, and is stored in a memory 35b'. The output signal of this memory 35b' is input to the image processing circuit 38b.

The output signals of the preamplifiers 32a and 32b are input to a light adjustment circuit 165, and are compared with an appropriate level by the modulation circuit 165 so that the amount of opening of the light source aperture 13 is adjusted by this comparison output for light adjustment.

In this second variant form, when the endoscope system is used in the normal-light mode, the RGB filter 21 of the switching filter 17 is withdrawn from the illumination light path, and the switching filter 143 is used with the first filter 143a which is positioned on the illumination light path.

The CCD drive circuit 31b applies the CCD drive signal on the color CCD 28c, reads the stored signal charge, converts the signal into a digital signal by the A/D conversion circuit 34b, executes color separation by the color separation circuit 164, then separates the signal into the luminance signal Y and the color signal C, and temporarily stores the signal in the memory 35b'.

The signal read from the memory 35b' is input to the image processing circuit 38b, where conversion into an RGB signal and contour highlighting are executed using the internal matrix circuit, is input to the D/A conversion circuit 39 after passing through the superimpose circuit 161, is converted into an analog RGB signal, and is output to the monitor 5.

In the fluorescent mode, the filter for fluorescent observation 22 of the switching filter 17 is positioned on the illumination light path, and in the switching filter 143, the second filter 143b is positioned on the illumination light path, and is used in the same way as the first variant form.

According to the second variant form, fluorescent images and normal-light images can be obtained using the scope 2E, which houses the image pickup device for monochrome image capturing and the image pickup device for color image capturing.

Different embodiments can be implemented by partially combining the above mentioned embodiments, which belong to the present invention.

For example, the endoscope system 1D in FIG. 26 may be used with a different scope. For example, a scope dedicated to normal-light observation 2c, which is the scope 2A wherein the excitation light cut filter 27 does not exist, may be connected, and in the case of this scope 2C, the control circuit 37 may execute a control operation similar to the normal-light mode by the CCD 28b of the scope 2B.

In the endoscope system 1A in FIG. 1, the scope 2A and the scope ID circuit (or model information generation circuit) at the 2C side may be installed, and the model detection circuit for judging (detecting) the model from the information of the scope ID circuit (or model information generation circuit) may be installed at the processor 4A side, so that the control circuit 37 executes control operation according to the connected scope 2A or 2C.

The embodiments, where the above embodiments are partially combined, also belong to the present invention.

Having described the preferred embodiments of the invention above by referring to the accompanying drawings, it should be understood that the present invention is not limited to these precise embodiments, and that various changes and modification thereof could be made by one skilled in the art without departing from the spirit or scope of the invention as defined in the appended claims.

What is claimed is:

1. An endoscope system which displays normal-light images by white light in a normal-light image mode and fluorescent images including fluorescent information in a fluorescent image mode, comprising:
  an endoscope which houses a monochrome image pickup device for capturing the images of reflected light and fluorescence from the body cavity, an excitation light cut filter which is installed in front of said image pickup device for shielding said excitation light, and an endoscope ID which includes information on the type of the endoscope; and
  a light source unit further comprising a first switching filter which includes a filter which irradiates light including excitation light for the fluorescent image mode and a filter for generating continuous light of red, green and blue (RGB) for the normal-light image mode, which are switched according to the switching of the fluorescent image mode and the normal-light image mode, and a second switching filter, which includes at least one limiting filter for limiting a part of the wavelengths of the excitation light of said first switching filter, and can switch said limiting filters according to said endoscope ID or observation state in the fluorescence mode,
  wherein said excitation light cut filter shields the excitation light generated by said first and second filters.

2. The endoscope system according to claim 1, wherein the filter for generating the excitation light out of said first switching filter includes a part of blue light (400 to 470 nm), and the second switching filter includes at least a filter which passes light in the visible region and a filter for shielding the shorter wavelength side or the longer wavelength side of blue out of said excitation light.

3. The endoscope according to claim 2, wherein the shielded excitation light is about 430 to 470 nm.

4. The endoscope system according to claim 3, wherein when the excitation light and leak light, other than the excitation light from the light source unit, is transmitted through the excitation light cut filter, the transmittance is set to optical density 4 or less in the visible light region.

5. The endoscope system according to claim 2, wherein the shielded excitation light is about 400 to 440 nm.

6. The endoscope system according to claim 5, wherein when excitation light and leak light, other than the excitation light from the light source unit, is transmitted through the excitation light cut filter, the transmittance is set to optical density 4 or less in, the visible light region.

7. The endoscope system according to claim 1, wherein said first switching filter further comprises a filter for fluorescence for transmitting light which includes the excitation light in the fluorescent image mode and a filter for normal-light use for sequentially generating RGB light in the normal-light image mode, which are installed concentrically and rotatably, and can move according to the mode.

8. The endoscope system according to claim 1, wherein the mode to indicate observation conditions is displayed on the monitor for displaying the fluorescent image or the normal-light image.

9. The endoscope system according to claim 1, wherein when the endoscope is in the fluorescent mode, a specific scope switch is assigned to switching.

10. The endoscope system according to claim 1, wherein the fluorescent image or the normal-light image is captured by a different image pickup device.

11. The endoscope system according to claim 10, wherein the focus number of an optical aperture installed in front of each image pickup device for capturing fluorescent images and normal-light images is smaller for fluorescent images.

12. The endoscope system according to claim 10, wherein the area per pixel of the image pickup device for capturing fluorescent images is larger than the area per pixel of the image pickup device for capturing normal light images.

13. The endoscope system according to claim 10, wherein a selector for switching the signals of the image pickup device is housed in the endoscope so that the fluorescent image or the normal-light images can be processed in a same processing circuit.

14. The endoscope system according to claim 10, wherein the fluorescent image or the normal-light images are processed by a dedicated processing circuit.

15. The endoscope system according to claim 14, wherein the processing circuit for said normal-light images corresponds to one or both of RGB and Y/C component signals.

* * * * *